(12) United States Patent
Baker

(10) Patent No.: US 12,226,198 B2
(45) Date of Patent: Feb. 18, 2025

(54) SYSTEMS AND METHODS FOR MEASURING CAPILLARY REFILL TIME

(71) Applicant: ProMedix, Inc., Portland, OR (US)

(72) Inventor: Steven D. Baker, Beaverton, OR (US)

(73) Assignee: PROMEDIX, INC., Portland, OR (US)

( * ) Notice: Subject to any disclaimer, the term of this patent is extended or adjusted under 35 U.S.C. 154(b) by 90 days.

(21) Appl. No.: 18/356,921

(22) Filed: Jul. 21, 2023

(65) Prior Publication Data

US 2023/0355122 A1  Nov. 9, 2023

Related U.S. Application Data

(63) Continuation of application No. 18/182,971, filed on Mar. 13, 2023.

(60) Provisional application No. 63/269,245, filed on Mar. 11, 2022.

(51) Int. Cl.
*A61B 5/026* (2006.01)
*A61B 5/00* (2006.01)

(52) U.S. Cl.
CPC .......... *A61B 5/0261* (2013.01); *A61B 5/0053* (2013.01); *A61B 5/6826* (2013.01); *A61B 5/6843* (2013.01); *A61B 5/7203* (2013.01); *A61B 5/725* (2013.01); *A61B 5/7264* (2013.01); *A61B 5/746* (2013.01)

(58) Field of Classification Search
CPC ... A61B 5/0261; A61B 5/0053; A61B 5/6826; A61B 5/6843; A61B 5/7203; A61B 5/725; A61B 5/7264; A61B 5/746; A61B 5/02028
See application file for complete search history.

(56) References Cited

U.S. PATENT DOCUMENTS

2017/0014075 A1* 1/2017 Morimura ............ A61B 5/0059
2021/0369124 A1* 12/2021 Sheridan ............ A61B 5/02028

FOREIGN PATENT DOCUMENTS

WO    WO-2014078859 A1 *  5/2014  ........... A61B 5/7264

* cited by examiner

*Primary Examiner* — Peter Luong
(74) *Attorney, Agent, or Firm* — McCoy Russell LLP

(57) ABSTRACT

An example device for measuring a digital capillary refill time (CRT) can include a wearable component, a processor, and an output. The wearable component includes a touch pressure element and an optical sensor capable of transmitting and detecting optical energy. The detector converts the received optical energy into an electrical signal that represents the optical energy incident on the optical detector. The processor is programmed to receive the electrical signal from the detector, determine the CRT based on the optical sensor data, and output the electrical signal or the determined CRT.

20 Claims, 16 Drawing Sheets

SYSTEMS AND METHODS FOR MEASURING CAPILLARY REFILL TIME

CROSS-REFERENCE TO RELATED APPLICATIONS

This application is a continuation of U.S. application Ser. No. 18/182,971, filed Mar. 13, 2023, titled "SYSTEMS AND METHODS FOR MEASURING CAPILLARY REFILL TIME", which claims priority and benefit from the U.S. Provisional Patent Application 63/269,245, filed Mar. 11, 2022, and titled, "SYSTEMS AND METHODS FOR MEASURING CAPILLARY REFILL TIME," which is incorporated herein by reference in its entirety for all purposes.

BACKGROUND

Capillary refill time (CRT) is the time taken for blood to return to an external capillary bed, such as under the fingernail, after pressure is applied to cause blanching (i.e., color loss via blood removal). CRT, regularly used or calculated by medical practitioners or caregivers, is an important indicator for various conditions including hydration, sepsis, trauma, hemorrhagic shock, and conditions affecting distal blood flow. CRT measurement can be done manually, with visual changes in color marking the blanching and refilled states.

Other devices and systems that measure CRT are overly complex in their approaches, increasing cost and reducing usability, particularly for a digit-wearable device that could be made for in-home use or as a low-cost, disposable sensor, for example used in a hospital setting. The devices and systems are deficient in regard to the inclusion of a force sensor in the digit part of the wearable device, which allows for linking the release of pressure (force per unit area) to the CRT timing (beginning of the CRT window). This deficiency generally precludes use of manual pressure application with these devices. Because pressure and force are directly related, application of force results in an application of pressure and release of force results in a release of pressure.

What is needed is a device or system to effectively and efficiently determine capillary refill time.

SUMMARY

This disclosure is directed to a device for reliably providing a digital measure of capillary refill time. Various aspects, such as maintaining a touch pressure, are described in the disclosure.

DETAILED DESCRIPTION

Figure 1A:
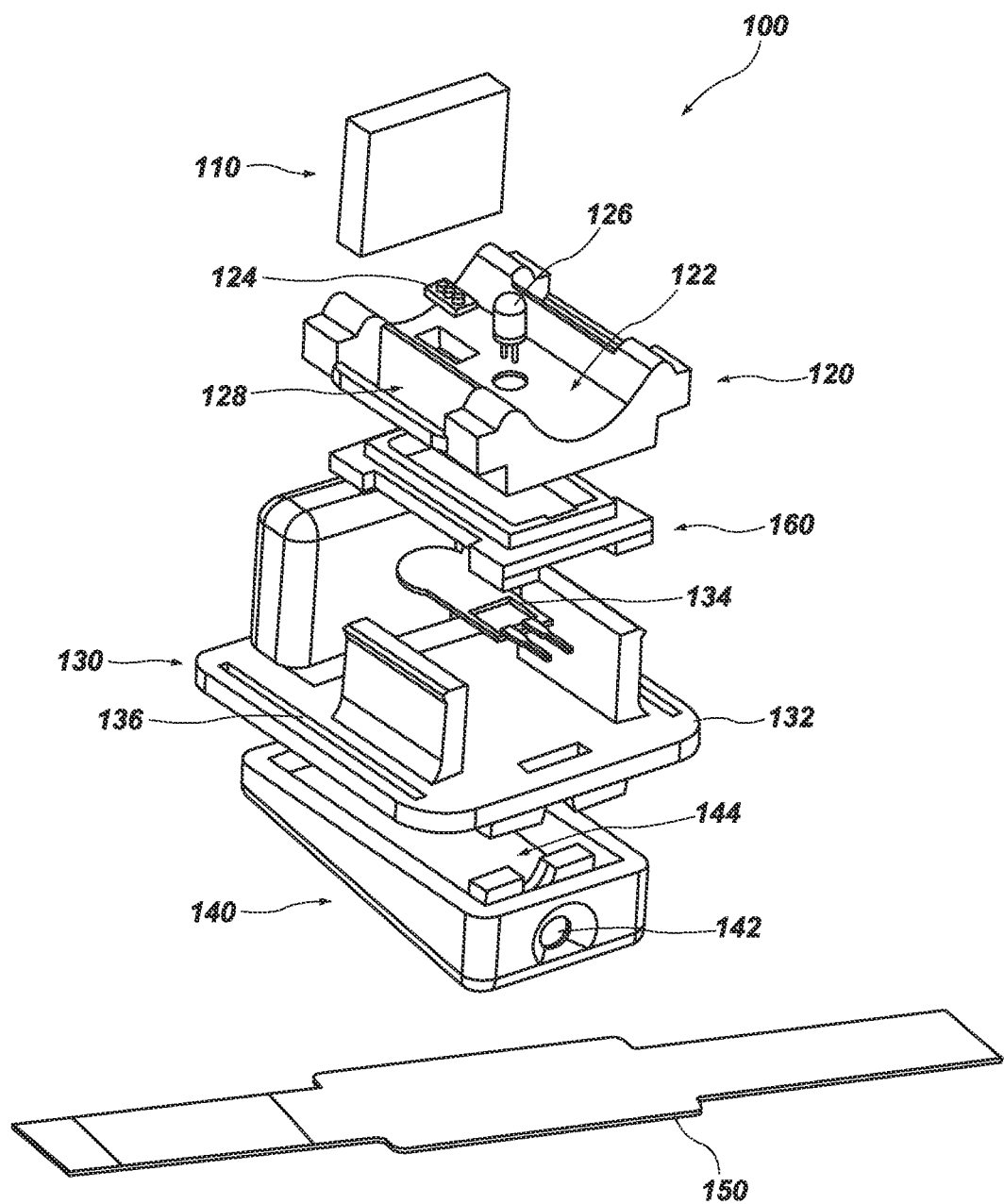
FIG. 1A is an exploded view of an example device.

Capillary refill time (CRT), whether alone or in combination with a vital sign or another physiological signal, is an important indicator for various conditions including dehydration, sepsis, trauma, hemorrhagic shock, and conditions affecting distal blood flow. The ability to accurately determine capillary refill time by medical practitioners or caregivers can be critical in properly evaluating a patient. Force application, force release, and determining a CRT start time can be crucial in accurately and properly determining CRT. Conversely, improperly, or inaccurately applying force, releasing force, or determining the CRT start time can render the CRT results invalid or inaccurate. An example, of inaccurately applying force is applying a force that varies significantly, e.g. by more than 20 percent, during the blanching interval.

CRT measurement can be made manually, with visual changes in color marking the blanching and refilled states, or with devices. Human measurements are typically made without a timer and have been shown to be unreliable. Devices offer improvements over manual measurement and observation. These devices utilize a variety of techniques, each of which involve inducing a blanching of the patient's capillary beds, typically in a digit or extremity, such as the foot, followed by optical (e.g., camera) or light-based (e.g., absorption, reflectance, or transmission) measurement of blood return to the capillary bed after pressure is released. In some cases, for example neonatal patients, the clinician may assess capillary refill time by blanching another area of the body, such as the skin atop the sternum.

Some of these devices rely on an automated mechanism to apply pressure to induce the blanching period. These mechanisms include pneumatic pumps that apply pressure to the digit in an automated fashion (e.g., via a pressure cuff). With a pneumatic pump, the pressure of the pressure cuff provides a measure of the force applied to the nail bed. However, rapid increase and rapid release of the pressure are limited by airflow rates. Another device includes a digit sensor that is capable of manual or automated (e.g., pump) application of pressure to measure CRT using light detection. That device does not describe a mechanism to facilitate accurate timing of CRT measurement using the pressure sensor in a manual pressure application scenario. Other conventional devices include a dual wavelength finger sensor and a foot sensor, which includes a force sensor in a floor pad to trigger timing in a CRT measurement.

Various example systems, devices, and methods for determining capillary refill time are described herein. The system ensures that an applied force is acceptable in both magnitude and duration. The applied force must produce a blanching pressure within the capillary bed. This may occur, for example, if the force is applied between the nail and the pad of a finger. The applied force may also be applied between the skin and body tissue, such as applying a force to the sternum. The force may be applied through a mechanical mechanism, just as a mechanism that supports an optical transmitter and receiver. The mechanical mechanism could be below the finger pad, above the nailbed, or both. The system also ensures that a duration over which the applied force is released or removed is preferable, acceptable, or unacceptable. These factors can establish that a capillary refill time determined or calculated therein is accurate. For acceptable force parameters, the system may be able to factor in adjustments to compensate for minor issues. Furthermore, the system can also determine that a deviation from an acceptable value or range or values, or an error in collecting or obtaining data, can require that the process be repeated to ensure that the capillary refill time is accurate. The system can consider the variation in successive measurements on the same patient to develop a reliability factor for CRT values. For example, if three CRT values are all within 10% of the average, the measurement might have a high reliability factor and if the CRTs vary by greater than 30% from the average, the measurement might have a low reliability factor, leading to a suggestion of repeating the measurement. The system can be used for critical care, in-hospital sepsis prevention, long term care detection of sepsis, dehydration management (e.g., in-home, pre-hospital, long term care, and in-hospital), the like, or combinations thereof.

A device generates an optical signal and a force signal. The optical signal is associated with light, having been emitted from an optical source, either transmitted through or reflected from a capillary bed of a digit (e.g., a finger or a toe) and received or collected by an optical sensor such as a photodiode. In this application, such an optical transceiver may be referred to simply as an optical sensor. Transmissive optical signals may be used as well. In this disclosure any mention of "optical signal" is intended to indicate either reflective or transmissive. For a green-light optical source (approximately 530 nm wavelength) using reflected light, the received optical signal is inversely related to the amount of blood flow in the distal capillary bed (e.g., more light reflected indicates less blood flow to the distal capillary bed; less light reflected indicates more blood flow to the distal capillary bed). A characteristic of the optical signal can be amplitude. Other wavelengths of light may be used, for example, red (approximately 655 nm) and infrared (approximately 940 nm). Green light generally provides the best signal to noise ratio for CRT measurements, while red and infrared wavelengths are used advantageously for detecting the fraction of oxygen-saturated hemoglobin relative to total hemoglobin (SPO2). The optical detector is shielded from the optical source so that optical energy is only detected for light that has been modulated by the body, for example by creating a wall between the transmitter and receiver. Further, the optical transmitters and receivers are protected from contamination and can be cleaned without degrading the sensors. A waterproof and chemical-resistant optical solution, such as one with glass covering provides these features.

The force signal is associated with force, which is determined by a force sensor, applied to, or exerted on the digit on or along a desired direction. A characteristic of the force signal can be amplitude. Alternatively, a force signal may be asserted if the force meets a minimum threshold. Such a signal may include hysteresis to avoid the signal de-asserting upon a small decrease in pressure after asserting.

The sensors convert the received stimulus (e.g., light or force) into an electrical signal (e.g., output current, output voltage, change of resistance, output current with internal gain, or the like).

The values of the optical signal vary over time due to fluctuations or changes in the light reflected through the digit. The values of the force signal vary over time due to fluctuations or changes in the force applied to or exerted on the digit. When viewed in combination, the optical and force signals can indicate critical points or elements for CRT data analysis, can provide data for CRT analysis or calculation, or both. For example, CRT is calculated as the time from force release to the time where the optical signal returns to a baseline value or within a predetermined range or percentage of the optical signal baseline, or when the slope of the curve reaches a predetermined value. The time duration release of force and the reflected light decreases (i.e., distal capillary bed is refilled) can be used to calculate CRT.

Analysis of the signals can be used to calculate CRT. Quality metric data can be used to determine whether the data has been accurately collected or whether the CRT measurement should be repeated. Quality metrics may be grouped several ways, including input and output quality metrics. Input quality metrics include features of the independent variables, such as the applied force baseline (force before the test), residual force, rise time, fall time, hold duration, constancy of the force during the hold duration, and the like. Output quality metrics include features of the dependent variables, such as the detected optical signal's absolute amplitude, change in amplitude, noise, monotonicity of optical signal increase as force increases, monotonicity of the optical signal decrease as the force decreases, constancy during the hold duration, and the like.

The optical signal varies substantially if an air gap develops between the fingertip and the optical sensor or if there is an air gap that varies during the test. In this case the waveforms tend to have a peculiar shape, which can be identified. However, using additional sensors, such as a fingertip contact sensor, the system can determine if the finger remained in contact with the optical sensor during the entire test and this input may be used either to disqualify waveforms where the fingertip contact with the sensor varied or where the fingertip was not in contact with the sensor at all. The fingertip contact sensor may be a mechanical switch. The fingertip contact sensor may also be resistive, capacitive, inductive, or optical. The system expects changes in the measured resistance, capacitance, inductance or optical signal that changes with the applied force. The change in resistance, capacitance, inductance or optical level that changes with the applied force may be used as a factor in determining the CRT.

The device provides a mechanism that permits release or removal of the applied force over an acceptable time period. In other words, the device can determine whether or not a force release duration is within a predetermined range.

The device is suitable for measuring CRT when placed on a digit of a patient, such as a finger or toe. Other form factors that are flat may be used to measure CRT on other areas of the body, such as the sternum. The device detects changes in the amount of light reflected from or transmitted through the digit to measure CRT. There is a baseline value of light reflection (i.e., light reflection through the patient's digit without application of a force) that is changed by application of a blanching force that removes blood from the digit and hence changes the detected light. After typically 2-4 seconds of constant blanching force, the detected light reaches a plateau value. After the release of the pressure within an acceptable time period (e.g., 5 seconds), the blood return to the digit and the detected light returns to the baseline value. The various embodiments of the CRT device are suitable for measuring and/or determining other parameters, such as pulse rate, peripheral perfusion, plethysmograph, perfusion index (PI), peripheral temperature. SPO2 and the like.

In this disclosure. CRT data includes all physiological measurements made and/or derived from the CRT sensor including at least: capillary refill time, oxygen saturation, perfusion index, pulse rate, digit temperature (ex: peripheral temperature), temperature gradients, differential CRT, differential perfusion. All CRT data may be included as part of the patient record and may be transmitted to an EHR server. During periods with no blanching, oxygen saturation may be derived using methods known to those familiar in the art if the optical transceiver includes IR and Red LEDs. From either the SPO2 or the Green plethysmograph, the perfusion index, which has been used as a surrogate for CRT, may be calculated from the ratio of the pulsatile (AC) to non-pulsatile (DC) signal levels. Note that a single sensor cannot measure SPO2 and PI while measuring CRT because the blanching pressure, the associated motion that occurs during the blanching period and capillary refill time, and the capillary refill itself adversely affect the SPO2 and PI measurement. Similarly. CRT cannot be measured while SPO2 and PI are active because CRT requires a blanching pressure. A system that includes SPO2 and CRT in the same housing must be able to select one or the other measurement to make and does so to optimize the reliability of the data and the patient outcome as described below.

Figure 13:
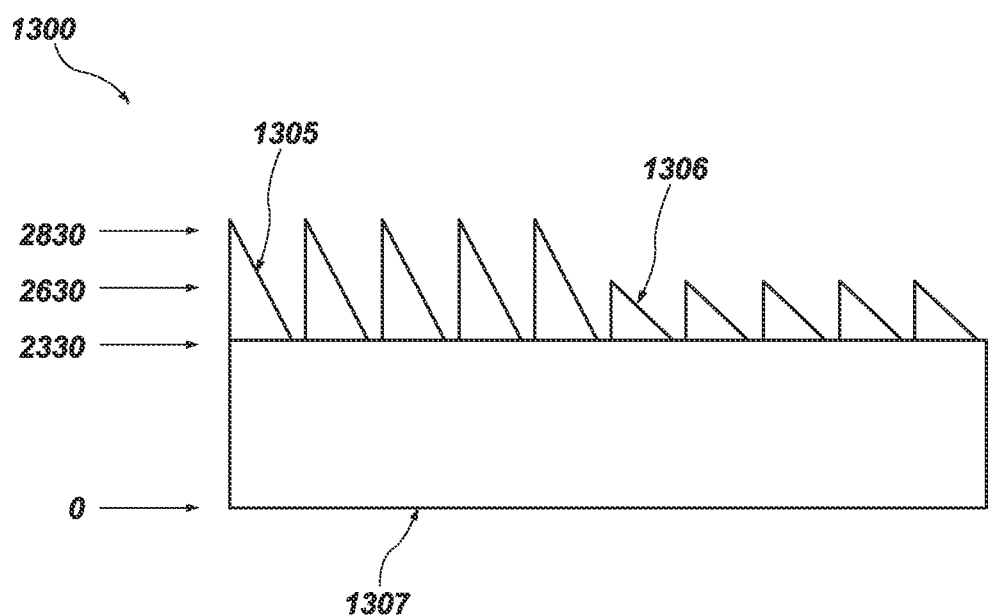
FIG. 13 is a schematic representation of a plethysmograph with varying pulse amplitudes and hence a varying perfusion index.

Referring to FIG. 13, a schematic of a pulse waveform 1300 suitable for determination of Peripheral Index is shown. The vertical height indicates the magnitude of the optical signal (arbitrary units) detected by a peripheral index sensor. Block 1306 represents the DC optical level, which depends on the amount of venous blood. In this example, the DC optical signal due to venous blood is 2330. Pulses that are visible in the plethysmograph and in each pixel of video are indicated schematically with large triangles 1305 having amplitude (2830−2330=500) and small triangles 1306 having amplitude (2630−2330=300). Larger pulses 1305 occur when there is a large stroke volume. Smaller pulses 1306 occur when there is a lower stroke volume such as occurs with hypovolemia, a symptom of sepsis, dehydration and other conditions. The perfusion index for the large pulses is 500/2330=0.21 while the perfusion index for the small pulses is 300/2330=0.13. The amplitude of the detected optical signal depends on the number of photons that strike the detector. Note that the amplitudes are ratiometric with the illuminating optical source. That is, doubling the optical signal doubles all the amplitudes and the PI is then independent of the amplitude of the illuminating optical source. Similarly, doubling the size of the detector (as long as the entire detector remains within the illuminated area), doubles all the amplitudes and PI is independent of the size of the optical detector. However, with a very small optical detector, such as a single pixel of an imaging chip, the amplitude may be very small for each pixel. The contribution of each illuminated pixel may be combined to increase the signal strength. In this way, the output of a video camera may be used to create a single "metapixel" and the output of this metapixel over time appears as a pulse waveform 1300.

A single sensor may have the ability to measure both PI and CRT, however, since CRT requires a blanching force, a single sensor can generally not measure the standard PI during the blanching period. PI measured during the CRT will provide a different value for PI than PI measured outside of the CRT. A sensor that measures both PI and CRT can provide the variation in time of the PI after blanching and may provide this as a metric. For example, the time it takes for the PI to return to normal after the blanching pressure has been released.

Separate sensors may be used to measure PI and CRT. Advantageously, these sensors are controlled by a PI-CRT processor running an algorithm that selects the use of one sensor or the other to optimize a variable, for example accuracy. Since CRT is the standard method for assessing peripheral perfusion, it is selected as the sensor when critical events occur such as initial assessment and assessment during the infusion of isotonic fluids. However. CRT requires the application of a blanching pressure, which requires either a clinician or a means to apply a blanching pressure, for example as disclosed in U.S. Patent Application Publication No. 20170209091, entitled Estimating Hydration Using Capillary Refill Time, which is herein incorporated by reference in its entirety.

An algorithm may use CRT to calibrate PI to CRT for a specific patient. PI is used when there is neither a clinician to apply pressure nor a means to apply pressure. PI is preferable when a continuous measure is required as PI is updated with every heartbeat. In contrast, CRT requires approximately 15 seconds between force applications to allow time for the capillary bed to refill. The algorithm may select CRT (either by indicating the clinician needs to provide pressure or by activating a pressure application means) when CRT or PI has changed a lot or is expected to change a lot (for example, when an input to the algorithm indicates that an infusion of isotonic fluids is occurring). The input indicating infusion of isotonic fluids may be entered manually, extracted from an EHR, and/or obtained by communication with an infusion pump. To save power and to provide a more comfortable patient experience, a system that has a pressure application means might select the use of PI when the CRT has been constant (perhaps no average change in CRT in the last 5 measurements). In this case, the algorithm might select a CRT measurement and immediately after the CRT measurement, select continuous PI measurements. The algorithm may select CRT measurements when the PI has changed substantially, for example, more than 25 percent. When PI has remained constant, the algorithm may occasionally select CRT to verify patient status is unchanged using the more reliable measure.

A separate system may cause a selection of a CRT measurement. For example if an updated estimation of patient's need to be admitted to the ICU, an ICT-estimation algorithm that requires a CRT measurement as an input, might communicate the need for an updated CRT measurement to the PI-CRT processor and the PI-CRT processor then selects the CRT sensor and either applies a force (if there is a pressure means available) or provides a message indicating that a clinician needs to apply a blanching pressure. The CRT sensor may also be connected to and/or have a CPU that communicates with other medical devices, e.g., a blood pressure sensor, vital signs monitor, or EHR for the purpose of obtaining the Mean Arterial Pressure. The CRT sensor and/or its connected CPU may be able to provide commands to other medical devices such as infusion pumps, e.g., to control infusion rate.

Using pulse detection algorithms that are familiar to those skilled in the art, the pulses may be counted over time, and from this count, the pulse rate is derived. The thermistor provides a measure of the temperature of the digit. By applying another CRT sensor to another digit, temperature gradients, such as between left and right side or between hands and feet, may be assessed. With a measure of core temperature from a device such as the WelchAllyn Sure-Temp thermometer, a core-to-peripheral temperature may be calculated. With CRT sensors on each hand, differential CRT and differential perfusion measurements may be calculated. That is, the sensor of the present invention may be used alone or in concert with other sensors to obtain CRT and other vital signs that are key to understanding the peripheral perfusion of the patient.

One or more algorithms that utilize CRT data, whether alone or in combination, can be implemented to determine CRT, determine one or more patient conditions associated with the CRT, or one or more treatments for the one or more conditions. The CRT data, having been collected by a CRT system, can be stored in and retrieved from the CRT system, an electronic medical record (EMR), a storage device (e.g., a hard drive or a server), or the like. The one or more conditions can be, for example, dehydration, sepsis, trauma, and conditions that affect distal blood flow.

An output of the CRT system can be a value, can be a qualifier (e.g., "good reading." "reading is accepted," "bad reading," "retry required." "re-measure." or the like), can be a determination (e.g., "CRT is in an acceptable range." "Check other vital signs." or the like), the like, or combinations or multiples thereof. For example, the output can be "Reading is good. CRT is 1.82 seconds." As another example, the output can be "Re-measure. Force release was improper." Items that are evaluated to determine if the reading is good/accepted or bad/retry required include the quality of the applied pressure and quality of the optical signal. Quality of the pressure considers: fast rise time (e.g., 100 ms), fast fall time (e.g., 100 ms), whether the blanching pressure is relatively constant (e.g., within +/−1 N), the blanching pressure (e.g., between 6 and 8 N), pressure duration (e.g, 4-6 seconds), amount of residual pressure after release (less than 0.5 N), and amount of pressure before blanching occurs (less than 0.5 N). Quality of the optical signal considers (values given are exemplary): if optical signal level is adequate, e.g., at least 1200 ADC counts; if the AC component of the optical signal prior to blanching is less than 120 ADC counts, if optical signal with blanching is at least 1350 ADC counts, if the shape of the optical signal after blanching is released approximates a falling exponential (for green light whose reflectance from the digit is detected), if noise on the optical signal during blanching and after blanching is less than 120 ADC counts, and if the optical signal returns to a clear baseline. Other qualifiers such as finger temperature, waveforms, quality metrics and the like, may be stored, included in the output, stored in the patient's medical record, included in log data, or the like.

For a simplified user interface, the output may provide an assessment of results using icons, for example: green to mean the CRT is good, yellow to mean the CRT should be re-measured, and red to mean the CRT indicates the patient may require additional treatment. Finger temperature may be used in conjunction with core temperature to provide a core-peripheral temperature gradient and also an ambient-toe temperature gradient, which have been shown to correlate with risk of sepsis. Temperature gradients can be used to distinguish between cardiac and respiratory causes of dyspnea (labored breathing). A core-to-peripheral temperature gradient of >8° C. was able to rule in a cardiovascular cause whereas one of <5° C. could rule it out. By applying a CRT sensor to a digit and obtaining a value for the patient's core temperature (for example, through an EHR interface and/or an interface to multi-parameter vital signs monitor that measures core temperature), the sensor may provide this temperature gradient. Similarly, with a measure of the ambient temperature, for example, the temperature from the CRT's temperature sensor prior to being applied to the patient's toe, the ambient-toe temperature gradient may be developed. Each of these measures may be provided as an input to a statistical. ML, AI, or other model that predicts probability of some condition, e.g., sepsis, or predicts the probability of a future condition or need, e.g., need for ICU admission.

As with many illnesses, multiple factors are used to diagnose and/or determine the appropriate treatment for sepsis, dyspnea, dehydration, trauma, hemorrhagic shock, and other conditions affecting distal blood flow such as peripheral artery disease and vascular surgery. Current algorithms that predict sepsis do not include capillary refill time and are weakened without this vital sign. For the CRT metric to have value, it must be an objective, repeatable measure, not a subjective or approximate measure as in typically complete as part of patient screening. In a typical patient screening, a clinician applies a blanching pressure to a finger, toe, or other area, releases the blanching pressure and without benefit of a timer, determines if the capillary refill time is slow or fast (typically in comparison to two seconds). For example, variability of capillary refill time among physician measurements, researchers found intra-physician measurements varied by 1500 ms or more 74% of the time.

In contrast, in the Andromeda shock and other clinical studies of CRT, a variation of 10% in CRT value was found to be clinically significant. In the case of the present invention, repeatable is considered to be successive measurements taken within 5 minutes that agree within +/−200 ms. A system should be able to screen out or compensate for variations of more than approximately 10% or 250 ms, whichever is larger, that are due to temperature effects, motion artifact, or an inappropriately administered test where the pressure or optical profiles are unacceptable as described above. A system that predicts sepsis including an objective capillary refill time will provide a more reliable predictor than the current models. Including one or more temperature gradients also improves the predictive strength of algorithms to determine if a patient has sepsis, cardiovascular causes for dyspnoea, success of vascular surgery, and the like. If it is the case that an increased temperature gradient has a strong correlation with increased CRT, then it can be that one may be used to check the other. This is particularly useful when quality of the CRT data is compromised, making it difficult to analyze. Examples include when the data have noise, or do not return to the pre-blanching baseline. That is, if the fingertip-to-core temperature gradient is small and the reported CRT is long, then we may conclude that at least one measurement is erroneous and the caregiver is prompted to repeat the measurements.

Conversely, if the temperature gradient is large and the reported CRT is long, the metrics confirm each other, indicating that the long CRT measurement is likely accurate. The match or mismatch between metrics can be used as part of an analytical model that determines the likelihood that a measurement has error. For example, perhaps without any temperature gradient input, the model suggests there is a 60% likelihood that an elongated CRT measurement is reliable. If the fingertip-to-core gradient is large and the fingertip-to-room temperature is small (both indicating poor peripheral perfusion), then the model's prediction of reliability might increase to 77% and the clinician is not prompted to re-take measurements. Conversely, if the fingertip-to-core gradient is small and the fingertip-to-room temperature is large (both indicating good peripheral perfusion), then the model's prediction of reliability might decrease to 42% and the clinician is prompted to re-take measurements.

Including CRT and other associated measurements such as room temperature, finger or toe temperature, temperature gradient, laboratory test results, core temperature, heart rate, respiration rate, depth of respiration, blood pressure, SPO2 level, patient demographics, patient history, and the like will likely improve algorithms to predict/detect and monitor sepsis, deep venous thrombosis, indwelling catheter thrombosis, dyspnea, dehydration, traumatic injuries, hemorrhagic shock, poor peripheral blood flow to extremities from any underlying pathology such as displaced fracture or crush injury, vascular surgery failure, and the like may include CRT and other associated factors. These algorithms may use heuristics, be derived based on statistical analysis and/or be based on artificial intelligence (AI) and more specifically, machine learning (ML).

Early sepsis diagnosis is difficult. Indeed, approximately 90% of patients who meet the SEP-3 inclusion criteria for sepsis are false positives. AI algorithms can be overfit and unknowingly trained incorrectly. For example, one sepsis detection algorithm's predicted probability of mortality increased with more data points entered. What the algorithm had learned is that people who are dying have more tests run and have vital signs measured more often. That is, the algorithm learned that more testing correlates with higher mortality rates and made predictions based primarily on then number of tests rather than the test results. However, adding digital capillary refill measurements to an AI/ML predictive algorithm provides a factor that improves the predictive model's performance. This valuable tool can be used to determine which patients are most in need of immediate, high acuity interventions.

To support machine learning and appropriate data pre-processing, data need to be labeled with critical parameters. For example, some optical CRT data may have cardiogenic artifact and would be labeled as such as an optical CRT waveform with cardiogenic data would be treated differently than a waveform with muscle artifact. In the cardiogenic case, the artifact only increases the optical value and this information is used to determine how the algorithm filters and/or replaces the artifact. In the cardiogenic case, the pulse might be removed and then that area of the plot is replaced with a smooth curve (matching the remaining values of the plot and at least 1st the derivative at the start and end of the replaced data). Data associated with a loss of finger contact, which may result in an inverted optical waveform (which literally appears upside-down compared to the normal waveform), are labeled to provide the ML algorithm a basis for detecting the inverted optical waveform in future data after the training sequence has been completed. An inverted optical waveform is one where some data have a force curve that rises too slowly, falls too slowly, or fails to have a constant force (pressure) between the rise and fall. These may be labeled as "bad pressure." The more the force application approaches a square wave, the more independent the CRT measurement is from the pressure. A rapid falling edge of the pressure waveform indicates the pressure was rapidly released. Consider the case where a rapid pressure release occurs and a CRT of 700 ms is measured. If the test were repeated, but with a pressure release interval of 800 ms, then some residual pressure would remain (and hence some residual blanching) would remain after 700 ms. The capillary refill cannot complete until the blanching pressure is fully released. In some examples, the pressure release time is less than one-fifth of the fastest CRT, or about 500 ms/5=100 ms.

Long blanching periods can affect the CRT and for this reason, knowing the blanching duration is helpful in evaluating the CRT. While it is possible to account for a slow application of the blanching pressure, it is easier (and perhaps more reliable) to remove this variable. A long period of blanching pressure application might by more than 10 percent of the blanching interval. Similarly, there are many ways that the blanching pressure can vary between the application and release. Keeping the pressure relatively constant, for example within +/−1 N helps ensure this variation is not a factor in the measured CRT Data that have the proper features and a timed capillary refill result may be labeled with "proper" and the CRT. The process of measuring the CRT (whether manually or automatically) and applying that label to the matching CRT waveform is fundamental to training a machine-learning algorithm. For example, a clinician may make a measurement with a CRT sensor to obtain a CRT waveform and another, visual measurement using a stopwatch, which provides the CRT label for the data. The data may also be analyzed to determine if each of the features and requirements are met and labeled as such. These labeled data may then be used to develop models that will predict the measured CRT based on a new set of data. The models may be based on machine learning, neural network, parametric equations, and the like. Models may also be based on statistical methods and regression models such as linear regression, analysis of variance (ANOVA), penalized linear regression, nonlinear regression, penalized nonlinear regression or multiple regression analysis.

For the purposes of monitoring patient health, a time series of data is used. The current invention can be used for trending CRT data through assistance of a clinician during regularly monitored vital signs. For example, with q4 vitals (vital signs measured every 4 hours), a clinician can press the digit to blanch at each standard interval for measuring vital signs. Vital signs include any physiological measurement such are heart rate, respiration rate, depth of respiration, quality of respiration, quality of pulse, systolic blood pressure, diastolic blood pressure, mean arterial pressure (MAP), core temperature, temperature of extremities, pupil reactivity to light, capillary refill time, peripheral perfusion index, height, weight. Lab results include results of any chemical analysis such as blood lactate levels, creatinine, bilirubin, and the like.

In another embodiment, the finger sensor includes a means to automatically apply pressure. One such example is provided by US Patent, publication number 20170209091 Estimating Hydration Using Capillary Refill Time, which is included herein by reference. In 20170209091, a pneumatic cuff is pressurized to blanch the nail bed and then the pressure is quickly released while an optical sensor interrogates the capillary blood volume. With a means to automatically apply and release pressure, a system may make automatic measurements of CRT parameters at any desired interval, for example every 15 minutes. The measurement interval may be fixed or variable. The measurement interval may be based on other vital sign measurements, a patient risk score, a prescribed time, on when other vital signs are measured or similar. For example, a doctor may have prescribed q4 (every 4 hours) vitals, but when the system detects an increased CRT and/or an increased heart rate, it may automatically begin measuring CRT and more frequent intervals. This invention included a system to automatically measure CRT at a prescribed interval and to adjust that interval based on patient state. Patient state includes vital signs, trends in vital signs, laboratory results, medications, demographics, diagnoses, and the like.

Patient state may be obtained from manual entry or through communication with a system such as an EHR. For systems that do not have a means to automatically apply pressure for CRT measurements, the system may include a notification to a clinician that the time interval has expired and instructions for the clinician to apply a manual pressure. Trending patient data allows a clinician to determine the efficacy of intervention measures. For example, after a fluid bolus is used to compensate for lost fluid, one expects peripheral capillary flow to improve. By measuring CRT over time, a clinician can see if the CRT is increasing, decreasing, or constant. The manual or the automatic CRT system may also include means to transfer the CRT data to another piece of equipment, such as a medical record storage database or patient monitor. In this specification, the term EHR is used to indicate any medical record storage database. An EHR interface may allow a device to both write data to and read data from the EHR. The means to transfer the data may be an HL7 interface, a Bluetooth Low Energy service, a proprietary interface, or another standard interface. When CRT data are transmitted to a second device, such as a patient monitor that is not an EHR, the second device may complete data transfer to an EHR.

Considering transmitting CRT data to a patient monitor, the CRT sensor and data may be integrated into a patient monitor in several ways. The CRT sensor may have a soft connection to the monitor, where it is an "add-on" sensor that may be attached to the patient monitor either via a cable such as USB or by a wireless connection following standards such as Bluetooth. Bluetooth Low Energy, Wi-Fi, Wi-Fi Direct, ZigBee. ANT, or other communication protocol. The CRT may provide data in the proprietary format of the patient monitor, as HL7 data, available to the monitor across an API and the like. The patient monitor may then include the CRT data with its own data stream to another computing device, such as an HL7 server, EMR server or EHR server. The CRT sensor may be integrated as a physical part of the patient monitor and under the same cover. The CRT sensor may be integrated with another parameter, such as SPO2 or blood pressure, as described elsewhere in this specification.

While there may be annotations in a patient record about capillary refill time being "acceptable", "less than two seconds", "prolonged", or the like, this invention includes the addition of a specific, objective value, such as 1.9 seconds, to routine vital signs and to the patient record. Unlike human-measured capillary refill times, this specific, objective value is determined by an algorithm such that the same data analyzed a second time will provide the same result. It further anticipates the inclusion of specific entries and/or support within proprietary, industry, and medical data APIs, such as HL7 and Bluetooth Low Energy services for CRT and its ancillary metrics and modifiers, such as PI, pulse rate, digit temperature, signal quality index, etc.

Medical devices that contain software, and particularly medical devices that support connectivity need to be secure at release and securable every day thereafter. Security includes preventing bad actors from accessing, blocking or manipulating the device, the network, or the data, and broadly entails authentication and encryption. Authentication is a way to verify that users and/or devices are who they say they are. Encryption is a method of encoding information so that it cannot be read by unauthorized entities. This device can recognize authentic sensors, for example, by using a digital signature or a Request/Response Encryption/Decryption/Verification protocol. Similarly, it can recognize authentic software upgrades by using a digital signature or by only allowing downloads from a known, secure site. With a network connected device, such as a smartphone as part of the system, the sensor and its firmware, the wristwatch and its firmware, and the software on the smartphone may all be verified as authentic. Locked-down versions of the smartphone may be used and secure communication to the smartphone may be used, for example by using RFID to support out of band pairing of the finger sensor and/or the wristwatch to the smartphone. The smartphone may support WPA2, WPA3 or other secure authentication/encryption means known to those familiar in the art. WPA2 and WPA3 both provide enterprise class authentication using 802.1x and also support the advanced encryption standard. The security system in this IOT device may meet the requirements for FIPS 140-2 and similar federal standards. The system may include out-of-band authentication as part of a method for providing a secure connection. For example, near field communication can be used to communicate a secret key for another wireless link, such as Bluetooth. Wi-Fi, ZigBee, ANT or the like.

When the output is a value, the practitioner or caregiver can incorporate the value with knowledge, other empirical or clinical data, or combinations thereof to discern or diagnose the condition of the patient. For example, if the CRT is less than 2 seconds, then the operator or practitioner can conclude that the patient has or does not have one or more medical conditions (e.g., is properly hydrated or does not have sepsis). As another example, if the CRT is 2 seconds or more, then the operator or practitioner can conclude that the patient has or does not have one or more medical conditions (e.g., is either not properly hydrated or has sepsis). As yet another example, the operator or practitioner can incorporate the numeric value with the patient's other data, including other vital signs, symptoms, or the like, so the operator or practitioner can determine the diagnosis or treatment.

By recording a repeatable, specific, and objective measure of CRT over time, a trend in the patient's progression can be seen, providing a measure of how the patient is responding to therapeutic interventions. Further, this measure may be used as part of a closed-loop fluid management system. For example, a patient may be septic with compromised peripheral blood flow and a low Mean Arterial Pressure (MAP). Without close-loop feedback, the attending physician might prescribe 30 cc/kg of normal saline over an hour and have a nurse re-check on peripheral blood flow and MAP every to determine if vasopressors should be added. With a direct measure of peripheral perfusion to provide feedback for an infusion pump, the physician could instead order, "Up to 30 cc/kg of normal saline until either the CRT decreases by 1-second or MAP increases above 65, at which point begin infusing vasopressors at a rate of 0.01 ug/gk/min." Including capillary refill time in the feed-back cycle provides an additional measure of the efficacy of the fluid bolus, vasopressors, and other interventions. This has the potential to reduce unnecessary IV fluids by helping the clinician decide when vasopressors may be preferred instead of fluids when the blood pressure is low. Closed-loop monitoring during fluid infusion monitoring may be used to measure efficacy therapy for other hyper/hypovolemia conditions, such as caused by dehydration or bleeding and help ensure the safety of patients at-risk for fluid overload, such as small patients and those with COPD.

The current solutions for infusion pump control of isotonic fluids, for example to treat sepsis, are limited by the subjective and inaccurate nature of CRT measurement. For example, the readings by two different clinicians on the same patient at the same time may vary by 6 to 8 seconds. Similarly, longitudinal measurements by the same clinician on the same patient (whose true CRT is constant) can vary 2-4 seconds. Assume a patient has a true CRT of 4 seconds. A first physician measures a CRT of 6 seconds and orders an IV infusion: normal saline 30 cc/kg over 30 minutes in hopes of reducing the CRT to 2 seconds. Higher rates of infusion are avoided out of concern that the infusion results in a hypervolemic patient. After 30 minutes, the true CRT has reduced to 3.5 seconds. After this 30-minute wait, if the subjective CRT estimate indicates that the CRT has reduced to less than 2 seconds, no more IV fluids will be infused. However, if the CRT is still greater than 2 seconds, then an adjusted infusion of 10 cc/kg will be given over 15 minutes. To further confound the problem, it is unlikely that the subjective CRT estimate is made at 30 minutes. With an objective, accurate, and repeatable measure of CRT, closed-loop infusion algorithm can adjust the infusion over the initial 30 minutes. For example, we expect the linear increase in the blood volume created by the infusion to create an exponential change in the blood pressure of the form $(1-\exp(t/\tau))$, where $\tau$ is a time constant that depends on the infusion rate. For an equation of this form, the system reaches 98 percent of its asymptotic limit in about 4-time constants ($4\tau$) and 99 percent of its asymptotic limit in 5-time constants ($5\tau$). Moreover, with a few measurements in the T/10 seconds, the asymptotic limit can be estimated to a high accuracy. Applying this to the instant invention, instead of waiting 30 minutes to determine if the infusion will result in actual CRT<2 s, the present invention will be able to determine within 1-2 minutes if the patient's CRT will reduce to seconds by the end of the original 30-minute infusion interval. If the algorithm predicts that the CRT will only reduce from 4 seconds to 3.5 seconds, then the algorithm may increase the infusion rate above the original 30 cc/kg.

Consider now the converse case where after 15 minutes of infusion at a rate of 30 cc/kg, the patient's true CRT has reduced to 2 seconds. In one embodiment, a predictive algorithm alerts the clinician that the time to reach the expected CRT is 15 minutes instead of 30 minutes. This allows the clinician to modify the infusion order. In another embodiment, the predictive CRT algorithm automatically adjusts the infusion rate so that after 30 minutes, the CRT is 2 s. Both embodiments have an advantage over current art in that they avoid over infusion and the resulting complications of hypervolemia.

The CRT system can also include an application, such as software or a set of firmware instructions that are implemented on a smartphone, a tablet, or a patient monitor. The application can be configured to relay instructions, outputs feedback associated with obtaining CRT measurements, displays CRT data, provides an explanation or summary of the CRT data, the like, or combinations or multiples thereof. In one example, the application provides instructions for obtaining CRT, including real-time feedback. The application provides instructions and feedback data to the practitioner for obtaining CRT measurements. It provides a user interface (UI) that indicates to the practitioner when to start applying pressure, how much pressure to apply, a graph of the applied pressure, and when to stop applying pressure. The application analyzes the applied pressure for the features described previously (amount of pressure and consistency of the pressure before, after, and during the blanching period, duration of the pressure, the rise time for applying pressure and the fall time for release of pressure.

Similarly, the UI indicates the optical signal level before, during, and after the blanching pressure is applied. The application determines if the optical trace has too much noise, too little signal, or has an abnormality, such as an inverted waveform, and if so, indicates a re-measurement is required. The application can communicate data for confirming a baseline or resting measurement, applying an appropriate amount of force, establishment of a plateau (blanching stabilization), determining a duration of release of force, the like, or combinations or multiples thereof. The application can also correlate or determine data associated with the CRT data capture, output CRT measurement, and conclusions drawn therefrom, including clinical estimations, measurement validation and quality metrics, or corrective instructions for CRT measurement repeat. If the algorithm to compute CRT is not overly complex, it could be implemented, albeit with a simplified user interface, on the same CPU that controls the sensor. In this case, a robust UI may still be implemented on an external computing device, such as a smart phone. The application may guide the user to take one or more than one measurement. CRT measurements may be supplied as numeric values and may be plotted. Plots may be a time series of the optical data and/or plots of the determined CRT values. Applied pressure may be supplied as numeric values and may be plotted. Plots may be a time series of the pressure data and/or plots of the average pressure applied during each blanching interval. Errors such as too much force, too little force, force not applied long enough, pressure was not removed fast enough, pressure was not applied fast enough, too much noise in optical signal and the like may be provided to the practitioner.

Figure 1B:
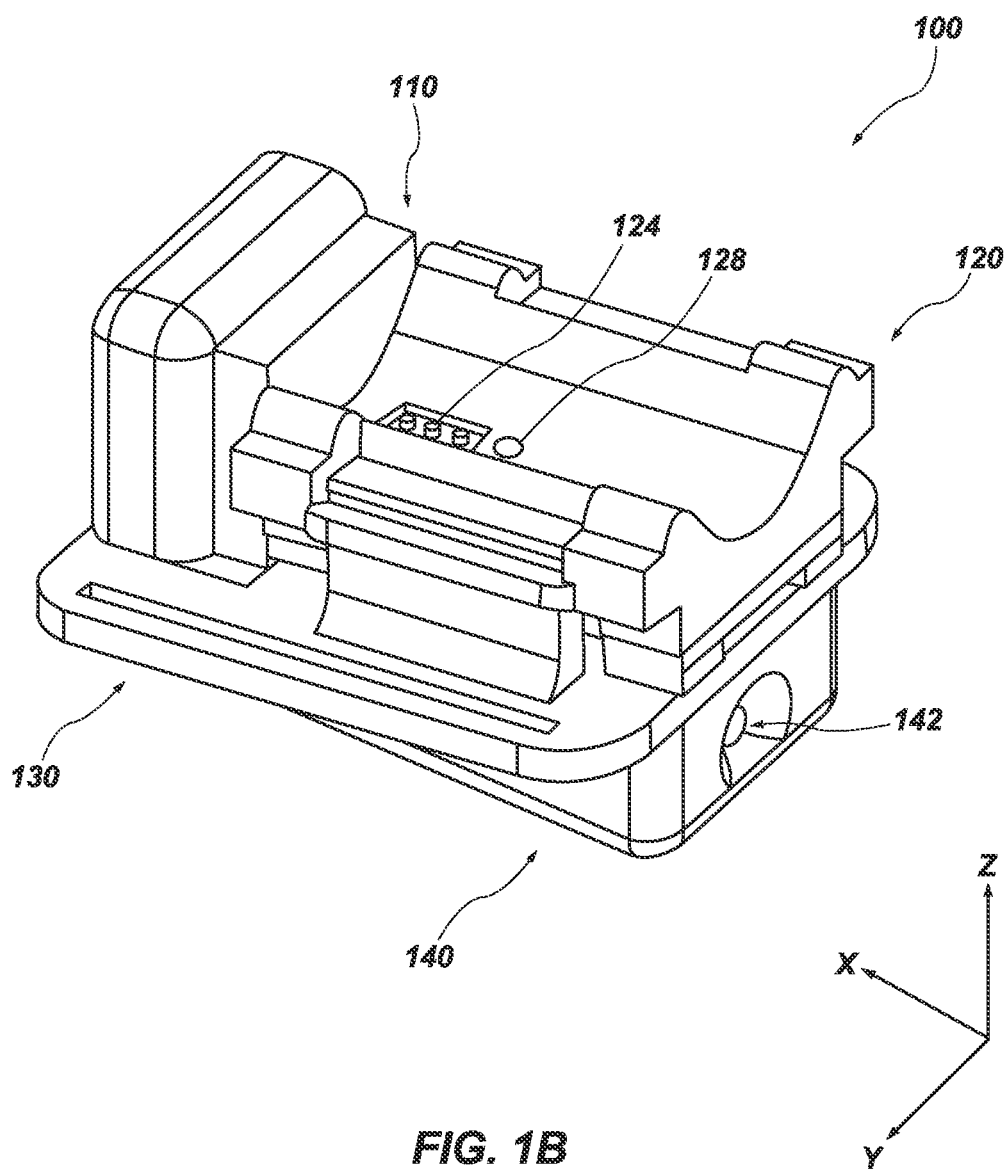
FIG. 1B is an isometric view of the example device.

FIG. 1A shows an exploded view of a device 100. FIG. 1B shows an isometric view of the device 100 having been assembled. The device 100 includes a digit plate 120, a base 130, and a connector 140. In the example shown in FIGS. 1A-1B, the device 100 can be worn in a free-form fashion (i.e., the device 100 does not need to be secured in or to a location, such as a tabletop). In another example, the device 100 can be a fixed, non-wearable device. The device 100 can be fixed to a tabletop.

The digit plate 120 includes a digit groove 122 to receive, accept, or support a digit (e.g., a toe or finger) of a patient. The digit groove 122 is concave. Alignment of the digit against, near, or proximal to an optical sensor 124 can affect testing and accurate data collection. Therefore, the digit groove 122 is sized and shaped to allow for accurate testing within a range of ages having varying digit sizes (e.g., the finger groove 122 of a first device is sized and shaped for babies, toddlers, and children ranging from 6 months to 10 years of age; the finger groove 122 of a second device is sized and shaped for children, teenagers, and adults older than 10 years of age). In one example, a diameter at an apex of the concavity of the digit groove 122 can be 8-18 mm, including, 10-16 mm, and 10 mm. An angle of a side wall of the digit groove 122 can be 20-70 degrees from a vertical axis, including 30-60 degrees, and 45 degrees. The digit groove 122 can have 0.1-2 mm of unevenness to prevent slippage of the digit within the digit groove 122. To help ensure contact with sensors 124, 202 and 605, these sensors may sit slightly proud, so that the fingertip touches the sensor slightly before contacting the digit plate. When designed for use on a relatively planar skin surface, such as the skin over the sternum or when the optical module 206 is disposed in a blood pressure cuff, digit plate 120 may be substantially flat. As used in this specification, a digit plate serves to hold some or all of the sensors. The functionality of the digit plate may be placed in part of the housing that is atop the nailbed and/or a part of the housing that is atop another part of the body such as the sternum, forehead, arm, etc.

The device 100 may also include a backstop 110. The backstop 110 includes a dent to accept a tip of the digit being received or supported by the digit groove 122, thereby aiding in digit alignment. The dent of the backstop 110 can be 0.1-10 mm, including 1-5 mm. The dent can be located in the center of the backstop 110 or can be offset from the center. The backstop 110 can be composed of a polymer or an elastic or flexible material, including, without limitation, rubber, silicon rubber, urethane resin, plastic resin, the like, or combinations or multiples thereof.

The device 100 may include a disposable adhesive covering 540 that removably adheres to the digit plate. This adhesive covering provides a clean surface for each patient and is placed on the digit-plate prior to each patient encounter and removed after each patient encounter. In another embodiment, the disposable adhesive covering has an adhesive on both sides, allowing device 100 to be removably adhered to the patient's finger, toe, or other skin area, such as over the sternum. Adhesive covering 540 includes features to assist in the alignment and removal of the adhesive covering. The system may include detectors (not shown) to ensure that the adhesive is in place before starting operation. The system may include different calibration constants, algorithms, and the like to include effects of the adhesive covering, such as increased thermal resistance and decreased optical clarity. Additionally, the adhesive removes the need for strap 150, which, if too tight, can create artifacts on the optical data. The adhesive may include a compliant layer, which helps ensure that the fingertip is held against the sensor. The covering may be a permanent or semi-permanent part of the digit plate. The digit plate may be constructed of a material, such as silicon, that is compliant and exhibits stiction. The disposable adhesive covering may include cuts, marks, folds, or similar methods to guide proper orientation.

Figure 1C:
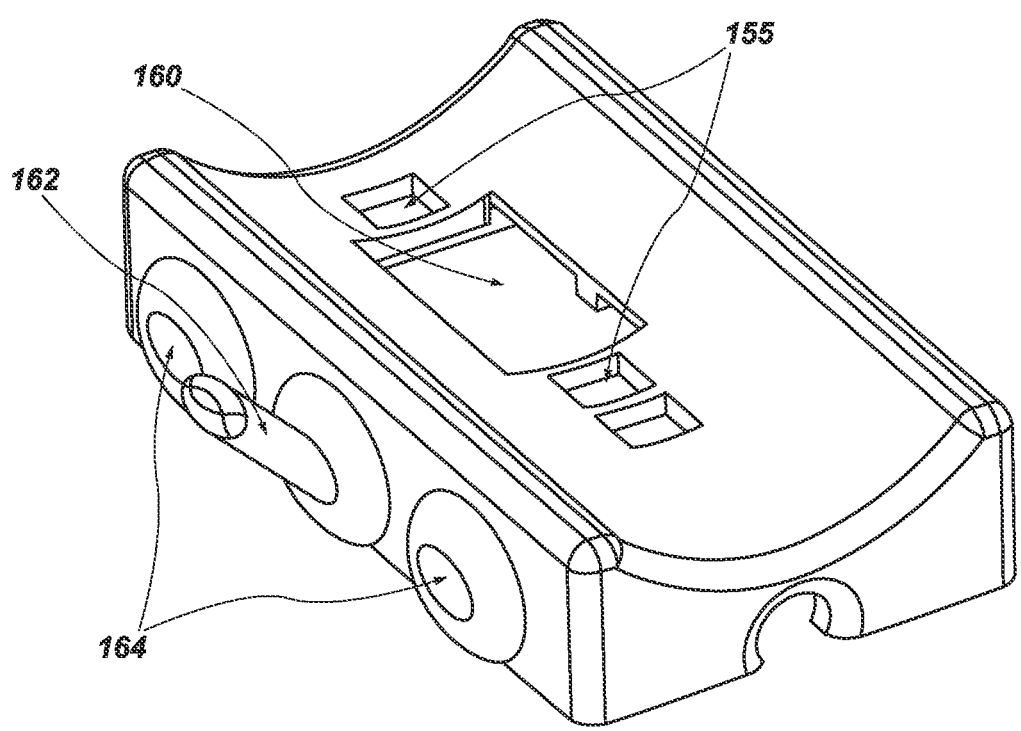
FIG. 1C is an isometric view of another embodiment of the example device.

The digit plate 120 also includes the optical sensor 124 to obtain an optical signal, thereby allowing for collection of baseline or resting data, blanching data, and capillary refill data based on the reflection light through the digit. The digit plate 120 may also include contact sensors that confirm the digit is in contact with the contact plate during the measurements as shown in FIG. 1C, which shows a simpler mechanical assembly. Contact sensors protrude through holes 155 such that a finger touching the optical sensor 124 that also protrudes through hole 160 will make contact with the contact sensors. Contact sensors may include mechanical solutions such as the Metrol BP4SWA precision limit switch that compresses upon finger contact or electrical solutions, such as contacts that connect to inputs to a comparator circuit as described in FIG. 6. Connectors 164 anchor strap 150, which then wraps around the patient's finger and is secured on hook 162. Ideally, when strap 150 is applied, it provides a touch pressure (nominally 0.1 to 0.3 N) that holds the optical sensor against the fingertip so that they are just touching with no air gap. Strap should not apply so much pressure so as to blanch the capillary bed. Both cases create artifacts (noise) on the optical data. Strap 150 is made of an opaque material that blocks ambient light from reaching the optical detector, in this example. Without application of touch pressure, several difficulties may arise. The first is that the baseline optical data is subject to more noise, for example due to motion artifact, ambient light, and/or a change in the optical transmission due to an air gap. The second is that upon release of pressure there is noise in the data for the same reasons. This noise may include a sudden change (a spike) in the optical data that has a similar magnitude as the optical change due to the optical pressure. This occurs especially when there is stiction between the fingertip of the clinician applying the pressure and the sensor.

The baseline or resting data is a value or range of values used as a fixed point of reference. The baseline or resting data can be calculated by sampling variations (i.e., changes or fluctuations in reflected light) in the optical signal over time. For example, the baseline or resting data can be calculated via a sliding window, whereby a window, having a width of a set length of time, evaluates a first set of data falling within the window, and the window is then slid to a second set of data.

Blanching is when blood flow to the distal capillary bed is reduced, thereby resulting in whitish color. Blanching is calculated by determining a stable optical signal (i.e., no fluctuation or fluctuation within a given window) when a force, applied to or exerted on the digit, exceeds a threshold, and maintains stability.

Capillary refill is the time it takes for blood flow to return to the distal capillary bed after blanching. Capillary refill time is calculated from the end of the blanching period to the time the optical signal returns to the baseline or resting value. Because measurement error tends to increase with lower signal-to-noise ratio and the optical signal decreases over time as the capillary bed is perfused with blood, the system may provide a more repeatable result when the time is measured from pressure release until the signal falls to some percentage of the original change from baseline to maximum value, for example 5 percent, which equates to approximately three time constants, as explained below.

In cases where there is noise and/or that the optical signal does not return to the baseline value, other methods may be used to determine the CRT. To determine the CRT, data are analyzed from a time before the blanching pressure is applied (typically 3-5 seconds) until up to 10 seconds after the blanching pressure has been released and the blanch-end criteria has been met. The data are more reliable if there is a touch pressure applied prior to the blanching pressure being applied and after the blanching pressure has been released. The signal may be filtered to remove cardiogenic artifacts and a curve may be fit to the data. For example, the Pade-Laplace method may be used to determine multiple exponential time constants associated with a decay. Knowing the decay time constant(s), a model may extrapolate to determine the CRT even if the optical signal does not fully return to the baseline. For example, data set that decays with time, t, according to $\exp(-t/T)$ will decay to within 37% of its final value in time $t=\tau$, to within 13% of its final value in time $t=2\tau$, and to within 5% of its final value in time $t=3\tau$. When compared to a person timing capillary refill, the instrument described herein is much more sensitive—for example, it can detect individual heartbeats based on minute variations in the optical response. Typically, about one decay time constant maps to the time that a person would manually measure.

An accurate measure of the response may include multiple decay time constants: $\tau 1, \tau 2, \ldots \tau n$, in which case the amplitude of each exponential element and each exponential element's time constant will factor into the CRT algorithm. The reason for multiple exponential contributions to the model are that there are multiple physiological processes that contribute to the capillary refill time: fluid pressure and fluid mechanics in arterioles, a different fluid pressure and fluid mechanics in venules, osmotic pressure for capillaries, which is impacted by the amount of interstitial fluid. All of these fluid reservoirs are emptied by blanching and when the refill at different rates, they affect the overall capillary refill at different rates. For example, if the interstitial fluid volume is 10× slower to recover than is the fluid in the arterioles and capillaries, then the capillary action after blanching has a is very different than if the interstitial fluid refills as fast as the blood in venules and capillaries refills. When multiple exponential elements with similar time constants and similar amplitudes are required to fit the curve, then no individual time constant can be used to accurately determine the completion time of the capillary refill. A single exponential is not capable of matching the overall curve. Only multiple exponentials with different time constants and amplitudes can match the overall curve. The Pade-Laplace algorithm may be used to determine these time constants and amplitudes.

Figure 14:
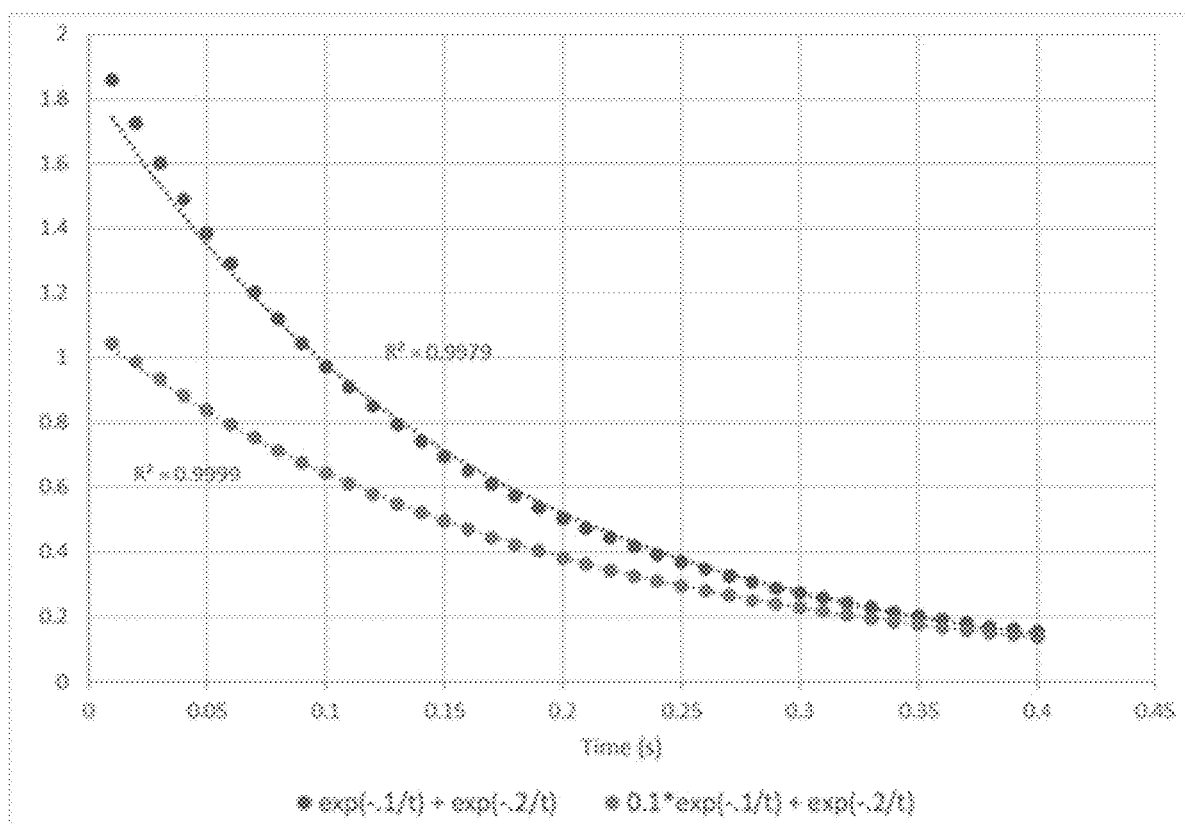
FIG. 14 is a plot showing two curves of summed exponentials.

However, if the amplitude of one exponential element is very small, for example one-tenth the amplitude of a second exponential, then the exponential with the smaller amplitude may be ignored as is illustrated in FIG. 14. The top curve is the sum of two exponentials with similar amplitude and the lower curve is the sum of two exponentials where one has one-tenth the amplitude of the other. Each curve has a single-exponential best-fit trend line shown with small dots. In the top curve, one sees that the trend line underestimates the actual data for times less than about 0.1 second and overestimates the data for times greater than about 1 second.

The optical sensor 124 can be a photodiode, a photovoltaic, a photoconductive device, a phototransistor, laser, or the like and may be an integrated optical module 206, including an integrated optical source(s) 126, such as an IR, Red. or Green LED, with nominal center wavelengths of 940 nm, 660 nm, and 530 nm, respectively. Light transmitted by the optical sensor passes into the capillary bed and is reflected back to the optical sensor having been modulated by the amount of hemoglobin the light passes through. The optical sensor 124 can be embedded in the digit groove 122, can be located in a strap 150, can be located between the digit groove 122 and the digit when rested on the digit groove 122, or can be located between the digit groove 122 and the base plate 132 with an aperture (not shown) extending through the digit groove 122 to permit the passage of light. The strap 150 is not included in FIG. 1B so as to not obscure any other elements or components of the device 100.

In one example, the device 100 can also include temperature sensor 202 to measure the temperature of the digit. Because low temperature in extremities causes vasoconstriction and increased capillary refill times, temperature may be used to adjust measured capillary refill times for temperature.

If red and IR optical sources such as LEDs are used by themselves or in combination with another color optical source, such as green, then the CRT sensor may also be used as an SPO2 sensor. During pressure application, the sensor detects the removal of blood from the capillary beds and upon pressure release, the sensor detects the refilling of the capillary bed. Application of pressure may be detected using a force sensor or by inspection of the optical signal vs time.

Figure 4A:
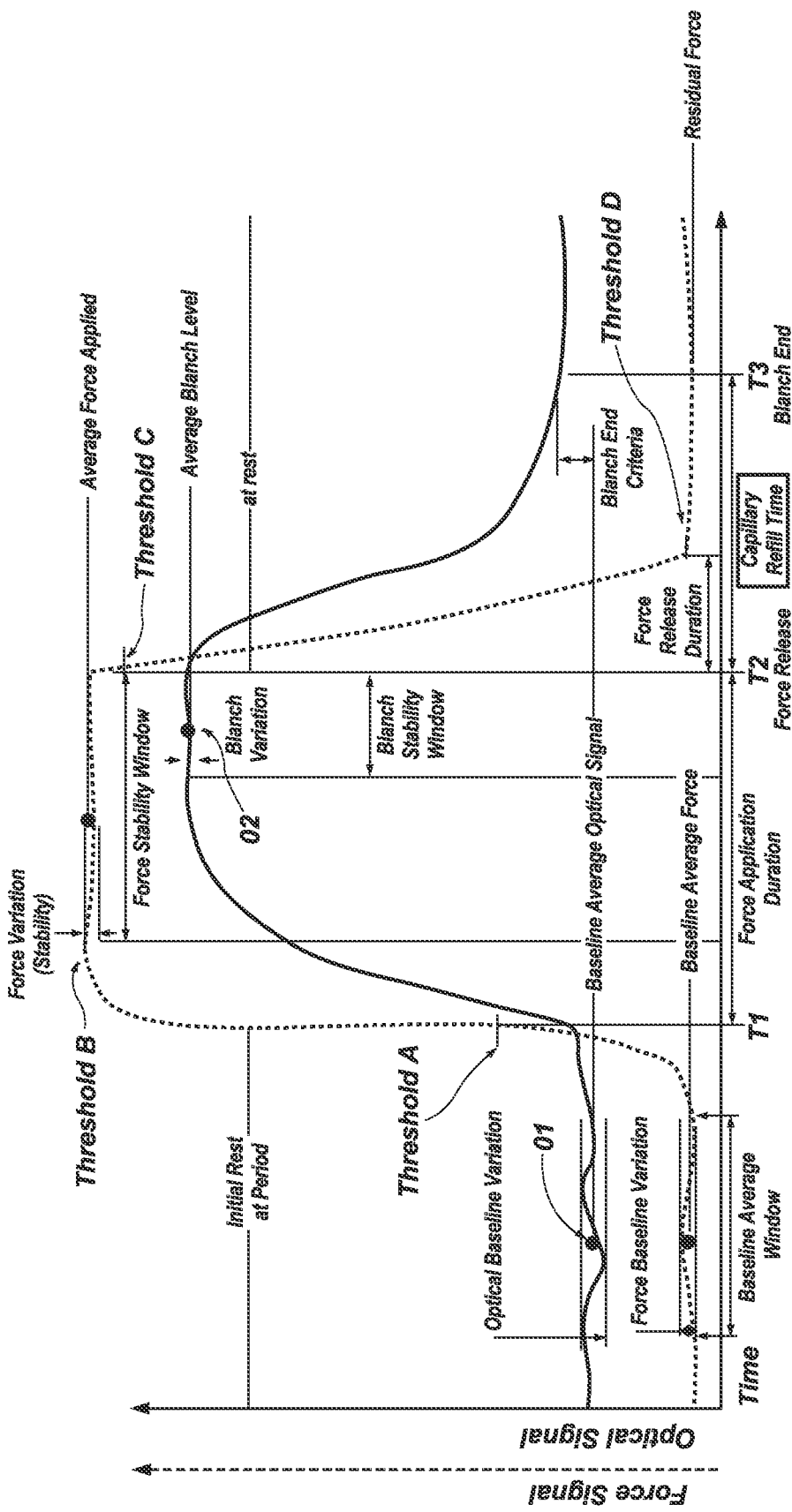
FIG. 4A is a plot of example data signals.
Figure 4B:
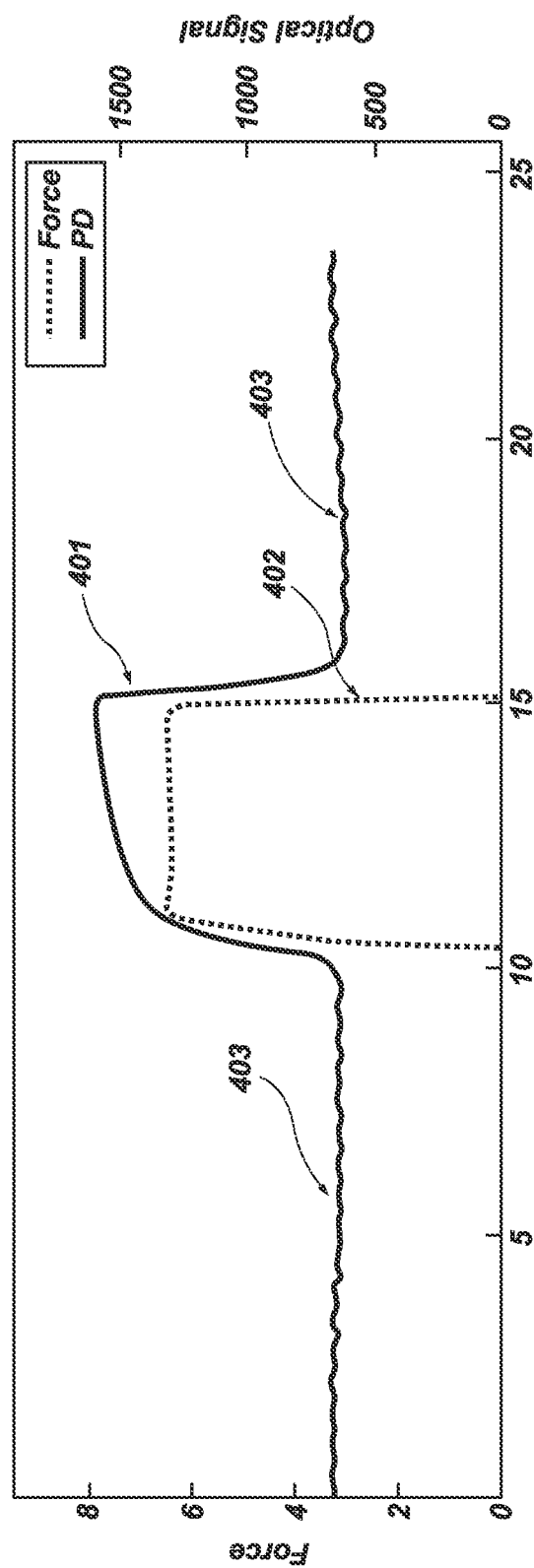
FIG. 4B is a plot of actual data signals.

For example, as shown in FIG. 4B the figure below, the optical signal increases as the increased pressure removes blood from the capillary beds. Once the capillary bed has refilled, SPO2 measurements may be made using the red and IR LEDs, using methods familiar to those skilled in the art. The force sensor may also be used to trigger an interrupt on a microprocessor, allowing the microprocessor to remain in a low-power state until the force passes a certain threshold, for example, Threshold A as described in FIG. 4A.

Analogously, with the addition of a blanching pressure, a sensor designed for measuring SPO2 may then be used to measure the raw data used to determine a capillary refill time. By analyzing the waveform and looking for a characteristic increase in signal as indicated in FIG. 4B, the system can determine capillary refill time without a pressure sensor. In FIG. 4B, the dashed line shows the force applied over time and the solid line shows the optical signal from the photodetector (PD). The x-axis units are seconds, force is in Newtons (N) and the optical signal is in ADC counts. Prior to about 10 seconds, the force is zero and the optical signal is constant, save for the cardiogenic artifact that creates small bumps in the otherwise horizontal data at about 600 counts. Just after 10 seconds, the force increases in a stepwise fashion and the optical signal also increases. The steep initial increase in the optical signal, followed by a curve and then a relatively linear increase is typical of the optical signal changes over time in response to an approximately constant blanching force.

At approximately t=-15 seconds, the force is removed and this force removal can be inferred by the sudden decrease in the optical signal at the point indicated by the arrow. It is therefore possible to determine an approximate end of force based on the time when the optical signal suddenly begins to decrease. This is true for an SPO2 sensor that has been squeezed to blanch the nail bed and also for a CRT sensor to which pressure has been applied to blanch the nail bed. The increase in the optical signal in response to the applied force is referred to as an "optical pressure response." Even with this ability to detect the release of pressure based on the optical pressure response, adding a pressure sensor to the SPO2 sensor supports more precise timing, feedback to the caregiver on the magnitude and duration of the pressure, and determination that the pressure was appropriate for an accurate CRT measurement. The reason that the optical pressure response has less precise timing is that there are physiological delays from when the force is removed until the optical sensor begins to change. This means that a CRT based on the optical pressure response will be shorter than one based on the force sensor. For physiological delays of only tens of milliseconds, this has no clinical effect, but at 100s of milliseconds, it does.

Similarly, because there is a weak physiological response to small variation in force, viewing the optical signal does not provide feedback to the clinician about the precise force level. A sudden force increase of 1-2 N just prior to release may affect the physiological response, and this would not be detectable in the optical signal, but it would be detectable in the force signal. Lacking the force signal, a valid CRT may be measured, though it may require more advanced algorithms to determine the validity of the data.

The amount of light reflected from the digit correlates to the amount of blood volume in the distal capillary bed (e.g., more light reflected indicates less blood flow to the distal capillary bed; less light reflected indicates more blood flow to the distal capillary bed). The optical sensor 124 converts the received light into an electrical signal (e.g., output current, output voltage, change of resistance, output current with internal gain, or the like). Additionally, the more light received, the greater the electrical signal generated by the optical sensor 124, and the less light received, the smaller the electrical signal generated by the optical sensor 124.

The digit plate 120 can also include one or more digit plate strap loops 128 to permit a strap 150 or portion thereof to pass through. In one example, the digit plate 120 includes two base plate strap loops 128, each base plate strap loop 136 on opposing sides of the digit plate 120.

The base 130 includes a base plate 132 to support a force sensor 134 and to allow for a physical connection to the connector 140. The force sensor 134 can obtain a force signal and measure force applied to or exerted on the digit within the digit groove 122 The force signal can be used to determine applied force for the duration of CRT, which can further permit the timing of pressure release (e.g., manual) to correspond to CRT initiation. A continuous pressure waveform provides a definitive input to determine the times at which pressure is applied and released. Perhaps most importantly a continuous sensor provides a measure of the time it takes for the pressure to be released. As mentioned elsewhere, if the time to release pressure approaches the time for physiological capillary refill, then the detected CRT will be erroneous as it will be a combination of the pressure release time and the actual CRT.

However, to construct a less expensive CRT sensor, one may use just the optical waveform to determine CRT. For example, when the optical waveform monotonically increases by at least 50% in less than 200 ms, we may assume pressure has been applied. A piecewise linear model of the optical data may be constructed. The initial rise of the optical signal may be approximated by a straight line and the intersection of that line with the baseline may be used as the start time. Similarly, when the force is released, the slow rate of increase of the optical data suddenly changes to a decrease. The last part of the increasing optical signal may be fit to a straight line and the first part of the decreasing signal may be fit to a straight line. The intersection of these two lines is the point where the pressure was released. Alternatively, the system may consider the value of the optical signal or the value of the first or second derivative of the optical signal to detect times of sudden change in the slope of the optical signal to provide the times for the application of pressure and for the release of pressure. The optical signal may be low-pass filtered, for example, to remove pulses from cardiogenic artifact, before determining the start and stop of pressure. Other methods may be used to determine the times of pressure start and release.

The force signal can also be used to determine signal quality measurements. Signal quality measurement data can be used to determine whether the force signal has been accurately collected or whether the CRT measurement should be repeated. For example, a force signal having too much fluctuation or variation, even if properly obtained, can render the collected data inaccurate or invalid. Typically, the force variation is caused by the clinician making the measurement. When provided a plot of the force vs time, trained clinicians are able to keep the force constant to less than 0.05 N, but without the plot, the force typically varies by over 1 N and may vary as much as 3 N on a target force of 7 N. Finger motion, particularly motion that results in pressure against digit plate 120 can also cause too much variation. If the clinician applies too much force before (after) the blanching period, then the pre- (post-) blanching baseline optical value will have an offset due to noise caused by pressure, and incorrect pre- and post-blanching baselines.

The base plate 130 can also include one or more base plate strap loops 136 to permit a strap 150 or portion thereof to pass through. In one example, the base plate 130 includes two base plate strap loops 136, each base plate strap loop 136 on opposing sides of the base plate 130. Baseplate 130 may pivot as a means to allow pressure applied to the baseplate 130 to be applied to an internal force sensor 134. Baseplate 130 may be made from a malleable or compressible material that allows a force applied to the bottom of the baseplate to be transmitted to an internal force sensor.

The strap 150 is sized to fit a digit of a predetermined size of patients. The strap 150 can be flexible, elastic, hook and loop fastener, the like, or combinations thereof. The strap 150 can be a single piece or multiple pieces. The strap 150 can form a side of the digit plate 120 opposite the digit groove 122. The materials of the strap 150 can block ambient light to increase or enhance the accuracy of light detection via the optical sensor 124.

The connector 140 includes a hole 142 and a cavity 144. The cavity 144 can include processing circuitry, modules, or both to process data signals, communicate with a secondary device, or the like. The hole 142 is sized and shaped to permit a wire or cable to connect the processing circuitry or modules of the device 100 to a second device (e.g., an intermediary device, a control unit, the like, or combinations or multiples thereof).

For example, the device 100 can communicate sensed data (e.g., force, light, and temperature) or processed data (e.g., CRT data) directly to a control unit (not shown) via an interface or output element (e.g., LED(s) or communication module) or indirectly to the control unit (not shown) via a wired or wireless coupling to another device (not shown), such as a wrist-worn module, a smartphone or tablet, or a patient monitor.

The construction of the device 100, including length (e.g. less than or equal to 12 inches including an intermediary device), weight (e.g., less than or equal to 5 ounces, including 0.37 ounces for the finger sensor), and attachment to the digit (including sticky and/or adhesive and/or soft/compliant covers), can reduce or eliminate one or more motion artifacts present in the optical signal, force signal, or both during CRT data acquisition. The concept here is that if the sensor has no (or very little mass), it has no inertia. With no inertia, the optical sensor tends to move exactly with the finger. Motion artifact tends to be generated when there is relative motion between a sensor and what is being sensed. If the sensor extends past the distal interphalangeal (DIP) joint, then bending the finger will cause displacement of the optical sensor, typically causing an air gap, which decreases the received signal. With the length of the finger sensor less than 25 mm, which is the typical length from the fingertip to the Distal Interphalangeal Joint (DIP) for an adult, the sensor moves with the finger, reducing motion artifact. In other embodiments, the finger sensor and the communication module are in a single housing or the finger sensor, communication module, and control unit are in a single housing, or the communication module and control unit are in a single housing. An air gap between the sensor and the fingertip creates noise as it significantly decreases the amount of reflected light that strikes the sensor and allows ambient light to strike the sensor. By having the optical sensor placed slightly proud (slightly above, e.g., 0.05 to 0.5 mm) of the digit plate (120), the optical sensor has a slightly higher pressure than the surrounding area. This minimally affects the blanching and CRT but reduces the chances that an air gap opens between the optical sensor and the fingertip. The addition of a compliant layer (not shown) with stiction atop the digit plate further reduces the chance that an air gap will form and tends to block ambient light from striking the sensor, even with the touch pressure reduced to near zero.

Figure 2:
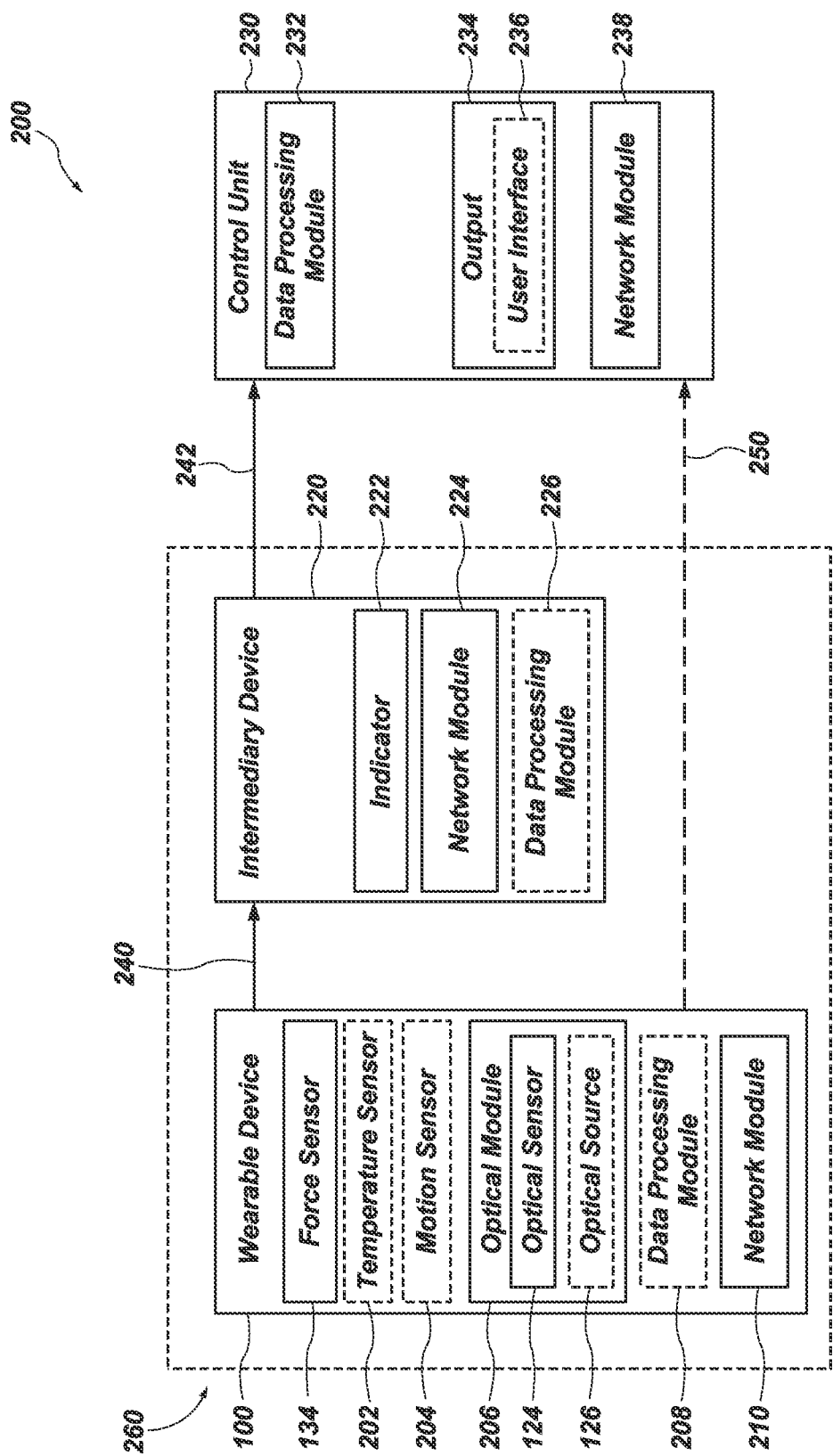
FIG. 2 is a block diagram of an example system.

FIG. 2 shows a block diagram of a CRT system 200. The CRT system 200 includes the device 100 and a control unit 230. The CRT system 200 can also include an intermediary device 220.

The device 100 includes the force sensor 134, as discussed above, and an optical module 206, which includes the optical sensor 124 and the optical source 126, as discussed above. The device 100 can also include temperature sensor 202 to determine temperature data of the patient's fingertip. As part of homeostasis, the body constricts blood flow to the extremities when it is cold. This restricted blood flow response is a healthy response to the body being exposed to the cold and it results in an elongated CRT for healthy patients who are simply cold. As part of homeostasis, the body tends to decrease blood flow in peripheral body parts by shrinking the diameter of blood vessels to maintain proper body temperature. A patient with cold fingers and with diminished blood flow to those fingers will have less blood flow to the fingers than if the fingers are warm. Because temperature can affect CRT, the temperature data can optionally be used in combination with the optical and force data to provide CRT or related determinations (e.g., using a relationship between temperature and CRT variation to scale a CRT measurement or determination derived therefrom, using the temperature data to validate or reject a CRT measurement, or the like).

There is little variation in CRT for digit temperatures between 22 and 38 C. The algorithm may reject, flag, or apply temperature compensation for CRT values measured when the digit temperature is outside of this range. Ambient temperature will be close to the temperature detected prior to applying the sensor to a fingertip or toe. When the ambient temperature is low, for example less than 20 C, the system may alert the clinician to consider if the ambient temperature has caused a low fingertip temperature. It is also the case that sepsis, which causes vasoconstriction, particularly in the extremities, can cause cold fingers. Septic patients have more fluid leakage into the interstitial space, which may also decrease capillary flow due to an imbalance in the hydrostatic pressure. If the temperature is too low, or to make a measurement without needing to compensate for temperature, or to confirm that the compensation for temperature is correct, the algorithm may suggest warming the fingers in warm (30 C) water and making additional measurements of CRT. Instead of rejecting or flagging CRT values measured when the digit temperature is outside the range of 22-38 C. the algorithm may compensate for the measured temperature and determine that even with this compensation, the CRT is excessive. For example, a patient with a digit temperature between 21-22 C may be expected on average to have a CRT that is 0.35 seconds longer than if the finger were warmer than 22 C. A measured CRT value of 3.8 seconds could be adjusted to be 3.45 seconds. Some studies show that the CRT of patients increases 3.3% for each decade of life. When the algorithm includes the patient age, then it may compensate for this factor as well. Compensation for cold fingers may be determined a priori by testing patients with various finger temperatures and determining a typical increase of the CRT with temperature. Other factors may be included in the temperature-correction model such as age, gender, skin color, finger size, prior history of arteriosclerosis, etc.

For example, testing can determine the typical increase in CRT for health patients as a function of age, weight, gender, and finger temperature. These data may be compiled in a look-up table which is referenced to apply a compensation in the measured CRT. For example, a CRT may be measured at 5 seconds on a 140-pound, 42 year-old, Hispanic male whose fingertips have a temperature of 29 C. The data in the lookup table indicates that for this ethnographic data and 29 C, the CRT is typically 1.8 seconds longer than for fingertips at a normal (33-37 C) temperature and the CRT is adjusted down from 5 seconds to 3.2 seconds. The algorithm may also include other temperature measures, such as forehead temperature, the room temperature and length of time the patient has been in the room, etc. Through statistical analysis, such as ANOVA (Analysis Of Variance), models for the effect of the various factors may be developed. Machine learning algorithms, including those that use neural networks, are able to consider the effect of factors across an enormous range of inputs and develop predictive models. Predictive models, such as the EPIC sepsis model (ESM, a penalized logistic regression model included in Epic's EHR) have little or no hope of making accurate predictions when the input data, such as CRT values, are provided inaccurately. Indeed, a retrospective study in JAMA Internal Medicine found that the ESM did not identify two-thirds of sepsis patients and frequently issued false alarms.

It is well documented that other vital signs, such as respiration rate, that require human timing are laden with errors. For example, a clinician may list all patients as having a respiration rate of 10, when in reality, these may vary from 6 to 15 breaths per minute. Models may use various inputs to assess probability, for example, the probability that a patient has sepsis, that a patient is dehydrated, or the like. Septic patients are given a Sequential Organ Failure Assessment (SOFA) score in 6 categories: Respiration. Coagulation Platelets, Liver Bilirubin, Mean Arterial Pressure, CNS GCS score, and Renal Creatinine. A change of 2 points in the SOFA is considered clinically significant. When values entered into the model have errors, then the SOFA score and thus the patient's risk level is computed incorrectly. The output of a model may be a score between 0 and 24, such as the SOFA score; a probability, such as an estimated risk of decompensation, a graphical representation, such as red/yellow/green, or other metric.

The device 100 can also include one or more motion sensors 204 to detect movement or motion of the device 100. The one or more sensors 204 can include a gyroscope, an accelerometer, the like, or combinations or multiples thereof. Movement or motion of the digit can affect CRT. Therefore, the motion data can optionally be used to indicate an error (e.g., when too much motion or movement occurs) or to account for blood flow variations due to the motion or movement. Gyroscopes not only provide motion sensing, but also tend to stabilize and minimize motion. As an example, data analysis may show that if an accelerometer records an acceleration of greater than 0.08 g, then there is a 95% chance that the data are unusable. In another scenario, where the hand is raised during the test, the motion relative to the heart results in a decreased pressure to the fingertips and therefore an elongated CRT based only on the change in position. Data analysis may show that then the height of the hand is increased by 10 cm relative to the heart, then the CRT increases by 20 ms on average. When a hand moves from the side to above the head, there may be a 50 cm height increase relative to the heart, in which case a there would be a position-induced increase of 100 ms in the CRT, which would be subtracted from CRT that was calculated from only the optical data.

The device 100 can also include a data processing module 208. One or more of the sensed data (e.g., force, light, temperature, motion) can be obtained as an analog signal. The data processing module 208 can convert the analog signal into a digital signal. The data processing module 208 can also process or analyze the sensed or converted data to obtain CRT determinations. The data processing module 208 can also receive and store the sensed or converted data.

The data processing module 208 can also filter, amplify, or filter and amplify one or more sensed data and can condition an output from the one or more sensors so the signals are represented by an analog voltage.

The device 100 also includes a network module 210 to transmit or receive communication to or from the intermediary device 220 or the control unit 230, such as via one or more connections, including over wired and wireless physical layers. In this specification, the term communication means is taken to include a system ranging from a simple communication means comprising the physical layer to a complex communication system comprising everything from the physical layer to the application layer. This includes for example, authentication, encryption, media access control, the network layer, and so on.

In one example, the device 100 can be connected 240 to an intermediary device 220 which, in turn, is connected 242 to the control unit 230. The connection 240 can be a physical or wired connection, such as via universal serial bus (USB), a cable or wire, or can be wireless, such as via a wireless protocol. The wireless connection or protocol can be infrared. Bluetooth. NFC. Wi-Fi, Zigbee, proprietary, or a combination thereof. The connection 240 allows communication between the device 100 and the intermediary device 220. Sensed data (e.g., force, light, temperature, motion) or processed data can be transmitted through the connection 240 to the intermediary device 220. The intermediary device 220 can then transmit the sensed or processed data to the control unit 230 via the connection 242, which can be physical or wired or wireless.

In another example, the device 100 can be connected 250 to the control unit 230. The connection, which can be physical or wired or wireless. 250 allows communication between the device 100 and the control unit 230. Sensed data (e.g., force, light, temperature, motion) or processed data can be transmitted through the connection 250 to the control unit 230.

The control unit 230 includes a data processing module 232 to process the data, calculate measurement quality, determine CRT result, the like, or combinations or multiples thereof. The control unit 230 also displays the results via an output 234 (e.g., display, screen, indicator, or the like), which can also include an output mechanism, such as a user interface 236 (e.g., GUI of a smartphone). In one example, the control unit 230 transmits data back to the device 100 or the intermediary device 220, e.g., for LED display. The LED display can indicate when a re-measurement is required and whether the measurement result is in an acceptable physiological range. The control unit 230 can then display or transmit the processed results, or portion thereof, to a user or practitioner. In one example, one or more functions of the control unit 230 can be implemented by the device 100.

The control unit 230 can also receive other physiological signals and information about the patient. The physiological signal correlates to a physiological or vital sign, including pulse rate, respiratory rate, blood pressure, blood oxygen levels, body temperature, the like, or combinations thereof. Information about the patient includes diagnosis, prescriptions, and ethnographic data such as age and gender. The control unit may apply these inputs to determine a risk for sepsis, for example by applying the patient information to a sepsis prediction model. The data and/or a projected risk for sepsis my result in the control unit modifying the interval for CRT (shorter interval if for higher risk for sepsis and for certain drugs, such as vasopressors, and when fluids are being infused). Body core temperature can be used to determine a differential temperature from digit to core, which may be used to determine if slow perfusion is due to hypothermia. The unit may further create an alarm, for example, if the CRT increases by 1 second over a time of 30 minutes.

The control unit 230 also includes a network module 238 to transmit or receive communication to or from the intermediary device 220, the control unit 230, or an external device, such as via one or more connections.

The CRT system 200 can also include an intermediary device 220, such as a wrist worn module, including one or more indicators 222 and a network module 224. The network module 224 transmits or receives communication to or from the device 100, the control unit 230, or an external device. The intermediary device 220 can include one or more indicators 222 (e.g., LEDs, screens, or the like), such as for data communication, feedback related to pressure application. CRT readings, errors, time, durations, alerts, notifications, the like, and combinations or multiples thereof. The one or more indicators 222 can also be used for a certain user population (e.g., LEDs that light up prior to and during measurement to distract pediatric patients). The intermediary device 220 can be worn by the patient, rested, or located on a surface, held by another person, or the like. For example, the intermediary device 220 can include a strap formed of an elastic or flexible material including at least one of rubber, silicon rubber, hook-and-loop fastener, urethane resin, and plastic resin.

The intermediary device 220 can also include a data processing module 232 to process the data, calculate measurement quality, determine a CRT result, the like, or combinations or multiples thereof.

The device 100 and the intermediary device 220 can form a single, integrated wearable unit 260.

The data can be processed to include additional data (e.g. age, gender, race, medical conditions that affect peripheral perfusion and/or temperature such as Reynaud's syndrome, ambient temperature, core temperature, temperature of fingers on the other hand, temperature of toes) or can be processed to apply to additional conditions or determined, such as producing pulse oximetry data, to make additional clinical estimations or recommendations (e.g., dehydration, sepsis, or the like).

Figure 3:
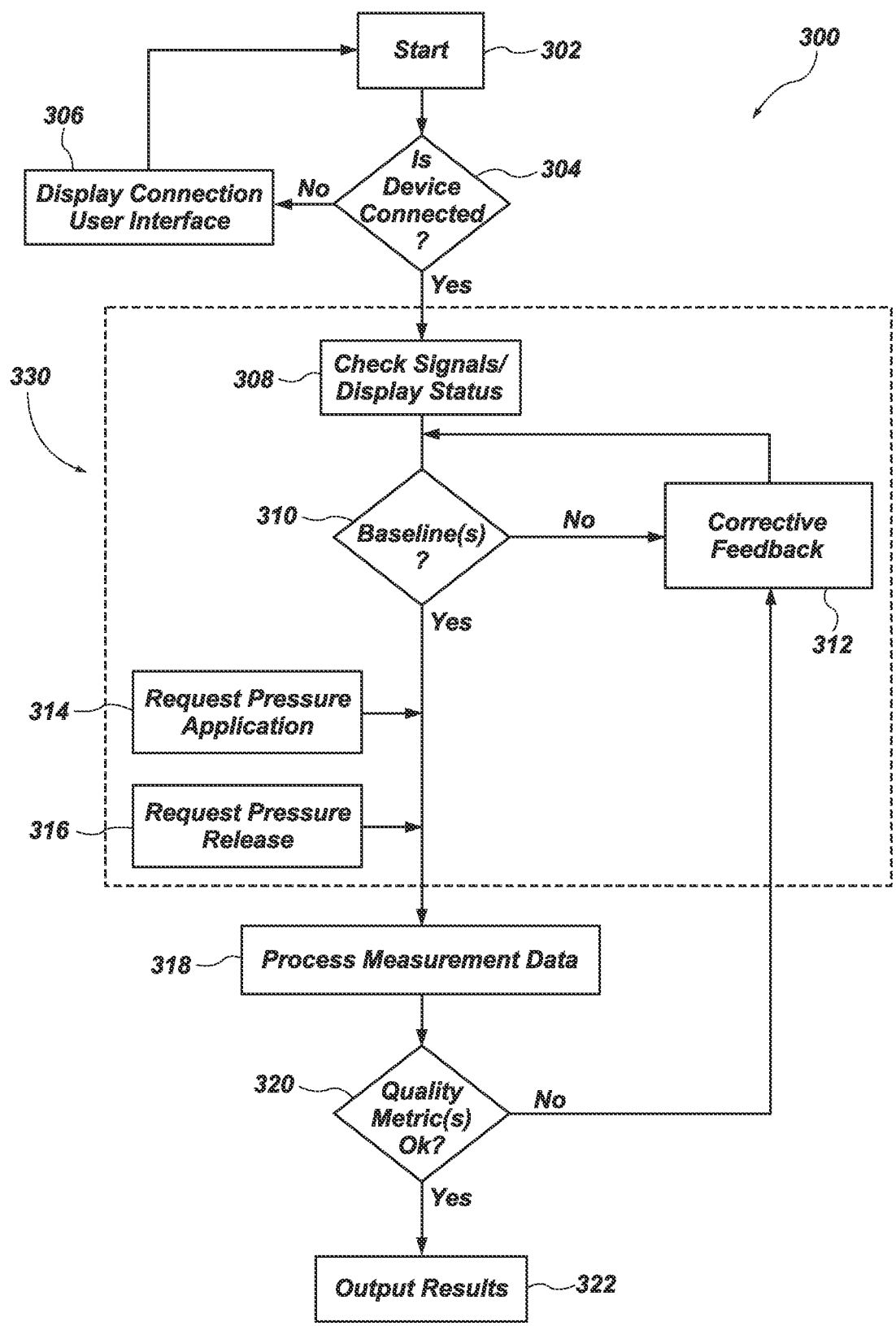
FIG. 3 is a flowchart of an example method.

FIG. 3 shows a flowchart of a method 300 for testing or data collection. At 302, the device 100 is turned on or the method is started. At 304, it is determined whether or not the device 100 is connected to the control unit 230. For ease of description and convenience, the control unit 230 is a smartphone running a CRT application. However, the control unit 230 is not intended to be so limited. For example, the control unit 230 can be a computer, a tablet, a laptop, an infusion pump, a patient vital signs monitor (e.g., a patient monitor), or the like. If the device 100 is not connected to the control unit 230, at 306, a connection user interface is displayed to assist the user with establishing the connection, such as via Bluetooth pairing or selecting a device for connecting. Furthermore, one or more control units can include one or more applications. For example, a smartphone of a practitioner performing the CRT test includes a CRT application. The smartphone application can include functionality for or output related to, without limitation, end user instructions, quality metrics, predictions, and linked information. A patient monitor application can include functionality for or output related to, without limitation, raw data signals or traces, CRT time, predictions, and EMR linkage. CRT data may be manually transferred from a CRT sensor to other devices. For example, a clinician may read the CRT value from a CRT sensor and enter that value into the user interface for an infusion pump, a patient monitor, an EHR, or the like.

Once connected, at 308, one or more sensors are checked to determine baseline signal data provided by the device 100. At 310, it is determined whether or not the baseline signal data and corresponding baseline measurements are acceptable. The data, measurements, or both can be displayed in a device screen, for example, listing detected force, optical and temperature data as real-time or live feedback 330.

FIG. 4A and FIG. 4B show a force data signal 402 (dashed or broken line) and an optical data signal 401 (solid line) resulting from the application and removal of the force. FIG. 4A calls out optical variation baseline O1, which is seen as cardiogenic artifact 403 in FIG. 4B. With consistent optical baseline, the system has a comparative baseline to define a blanch end criteria. A stable baseline has an slope of near 0 (averaged across a time that would ignore artifact 403, for example) and a variation that is small and constant, such as is depicted in FIG. 4A and FIG. 4B. Sudden changes in the baseline are due to noise that may be from motion that may cause separation of the finger pad from the optical sensor that decreases the optical signal that is due to physiological variation and increases the optical signal that is due to ambient light. A consistent baseline signal such as seen from approximately 0 to 10 on the horizontal axis indicates that a proper touch pressure has been applied. When this touch pressure remains at the time of force release, the optical sensor remains in contact with the skin.

In an initial rest period, the following data is collected by the optical sensor 124 and force sensor 134: optical signal changes prior to force application at T1 (a measurement of baseline optical stability or variation) and a force prior to T1 (a measure of baseline force stability or variation). The data is obtained to determine force and optical baselines. The data can also be obtained to ensure the quality of the CRT measurement. For example, the force variation in the initial rest period is expected to be less than 0.5 Newtons (N). This level of variation is expected, as the device 100 is free-form. Furthermore, optical stability is expected to be in the range of +/−10% due to the blocking of ambient light by the strap 150 and overall device construction, even when the device is moved about. If the force variation during the initial rest period is more than about 0.2 N, then the system may require the test be repeated because the quality of the baseline data is compromised.

Prior to T1, the force baseline is established. In one example, the force baseline is established by sampling force variation over time. A sliding window can be employed, whereby a window evaluates a first set of data falling within the window, and the window is then slid to a second set of data. The window has a width of a set length of time. The first and second sets of data can have at least one overlapping subset or individual piece of data, or the first and second sets of data can have no overlap. The window can have a width of 200-500 ms. As another example, the average force signal from a time prior to force application (e.g., 100-5000 ms prior to T1), can be stored for later processing use. Variation of the force signal within the baseline average can be calculated, such as by tracking the highest and lowest value of the force signal within the baseline averaging period (e.g., 100-5000 ms).

If any of the baseline data is found to be insufficient, corrective feedback, at 312, can be provided. For example, a force was not applied long enough, a temperature is too high or too low, too much movement or motion, or the like. Further details related to the corrective feedback may be given, for example information indicating that a longer pressure application is needed for force stabilization, achieving an adequate blanching period or blanching stabilization, or the like. This additional or different information can be desirable for different user populations (e.g., clinicians or other hospital personnel).

Feedback provided can include, without limitation, data indicating that a CRT test has or can begin, baseline measurements are obtained and are valid, an instruction to apply a force, a time or duration for which the force is to be applied (e.g., 3 seconds). The feedback can be visual, such as by visual indicators to provide real time or live feedback to demonstrate whether or the force application is at an adequate level, maintained for an adequate time, and that blanching has been achieved and maintained. Other live or real time feedback can be given, (e.g., an instruction to release the pressure at an appropriate time). Furthermore, alternative, or additional data presentation formats can be utilized, including as traces or other graphics. Feedback can also display acceptable boundaries for force data, optical data, or both, which can be provided in real time or live feedback.

The operator feedback is provided to permit the operator to perform the test within desired or acceptable ranges or values. For example, when an operator is applying force to the patient's fingertip, the operator feedback, whether in visual, audio, or optical format, can signal to the operator to increase or decrease the force applied. The operator feedback can also be provided to signal to the operator to perform the next step in the test. For example, when the operator is applying force, operator feedback can be provided, whether in visual, audio, or optical format, to remove the pressure once desired blanching has been achieved.

User feedback can also be provided. User feedback can include a determination that the device is too tight or too loose, that the optical source or detector are not positioned properly on the patient, or finger temperature. The above conditions can affect CRT or collection of information for proper determination of CRT.

Post-event data can be provided to analyze where an error occurred so an operator can correct that action in subsequent tests. The post-event data can also be provided for training purposes or performance evaluation. For example, if an operator consistently applies too much force, the device may require, after 3 tries, that a new operator be used. The post-event review data may include pressure and optical waveforms with marks indicating the detected start and end of pressure application and the time where the end of the capillary refill period was detected. It may provide a comparison against a standard waveform to allow the user to evaluate the quality of the CRT measurement. The post event review may allow the user to reject some data, for example when the user evaluation indicates the data is of poor quality or when the detected times are deemed inaccurate. The review may also provide specific feedback to the user regarding how to improve the technique to achieve a higher quality measurement.

Returning to FIG. 3, if the baseline data is adequate, application of a force is requested, at 314, and thereafter removal or release of the force is requested, at 316. In one example, the force is applied manually, such as by the practitioner.

At 318, data resulting from the application and removal of the force is measured and processed, including being analyzed by an algorithm. The data, such as that collected as discussed in FIG. 4, can be analyzed to obtain, or determine one or more results.

At 320, quality metrics of the optical and force signals are checked, such as to confirm force and blanching stabilization, and acceptable force release duration. If the quality metrics are determined to be invalid, corrective feedback 312 can be provided. If the quality metrics are determined to be valid, results may be displayed, at 322. Examples of quality metrics that may require corrective feedback include: optical data too low (for example less than 10% of full scale so there is insufficient resolution), optical data too high (for example exceeding the dynamic range of the ADC), force too low (less than 4 N), force too high (more than 9 N), force not constant enough (not within 0.5 N), force change of more than 0.3 N in the last 100 ms of the force interval (while the entire force interval matters, the force at the end of the force interval affects the CRT more than the force at the beginning of the interval), if the fall-time of the force (time after T2) is longer than 100 ms, waveforms that fall outside of the normal morphology, for example when the optical data decreases when the force is applied.

Returning to FIG. 4, at time T1, a force is applied, such as via manual pressing on the patient's digit. The applied force is measured or sensed by the force sensor 134 (e.g., a force sensing resistor). The time from T1 to T2 represents a duration over which the force is applied. The force application duration is the detection of the applied force over a first threshold level (Threshold A). T1 indicates the start of the applied force and the beginning of capillary blanching. T2 indicates the time at which the applied force, having been removed or released, is reduced to Threshold C and the beginning of a CRT window. In other embodiments, minimum and maximum force detectors may be used to determine when the applied force exceeds a minimum threshold and that the applied force remains between the minimum and maximum levels for the duration of the force application.

The force signal is used to identify the time (T1) when the applied force reaches Threshold A. This is the threshold where the applied force provides substantial blanching and may be a force of 1 to 1.5 N. The force signal is also used to identify the time (T2) when the applied force is removed or released and reaches Threshold C (i.e., the lower bound of the force stability window). During the time interval of T1 to T2, the force and optical signal characteristics are examined, such as with a sliding window, to determine measurement quality characteristics, including application of a sufficient or acceptable force level (i.e., achieving a force within the range of Threshold B and Threshold C) and the stability of force application (i.e., maintenance of a relatively stable (constant) force (e.g. +/−0.25 N) within the threshold range for a sufficient duration). The sufficient or acceptable force level and the stability of force applicant provide acceptable blanching. In other words, the applied force should exceed a predetermined amount (e.g., Threshold C), and should be maintained within a range (between Thresholds B and C) for a period of time (i.e., the force stability window). Threshold C can be 50-99% of the average force within the force stability period, including 90%. The width of the force stability window can be 100 ms to 10 seconds (s), including 500 ms, 1 s, 3 s, or the like. A force stability window that matches a typical clinical use, e.g., 1-2 seconds, may be used in a clinical use setting. It is difficult to maintain a constant force for a long period of time, for example, due to fatigue.

In one example, Threshold A is higher than the maximum value of the force variation in the initial rest period and lower than Threshold B, which is equal to the maximum force applied. Threshold C is lower than Threshold B and higher than Threshold A.

In one example, such as for teenagers or adults, the applied force application can be in the range of 1.5-4.0 N. In another example, such as for children, toddlers, and babies, the applied force can be less than the applied force for adults or teenagers. When the blanching force is very high (more than perhaps 10 N) and/or very long (more than perhaps 10 s), there is an increase in CRT that is due to the force and duration. The algorithm may either reject over-pressure and over-time blanching pressures or the algorithm may compensate for over-pressure and over-time blanching. While the first option is used because it considers the most precise answer, particularly in clinical settings, time is critical. If the measured CRT can be adjusted to compensate for errors in application, the device is easier to use and may take less time overall to provide a CRT that is correct (or within an error that is small enough to be clinically insignificant). For example, if the pressure is applied at a 15 N force for 5 seconds, the algorithm may adjust the reported CRT interval down by 720 ms compared to the measured CRT interval.

The force signal can be processed to determine the level of force application (e.g., directly via the device 100, the intermediary 220, the control unit 230, or combinations thereof), which can be reported as live or real-time feedback (e.g., via an LED or a user interface, such as an application or program). This aids the user or practitioner in applying the proper level of force to achieve blanching. This also aids the user or practitioner in avoiding patient discomfort.

Once a target range of force has been achieved, the force signal from the force transducer 134 is further examined to determine stability. That is, "Is the force application approximately constant?". The ideal force curve. F(t) can be described in terms of a Heaviside function, H(t). $F(t)=5*\{H(t)-H(t-3)\}$. In other words, a force of 5 N begins at $t=0$ and ends at $t=3$ seconds. The force stability is the maintenance of a force within a threshold range for a sufficient duration. The force stability is determined by the variation (e.g., a value, a range or values, or a percentage) in applied force over a given period of time. This can be thought of as the "AC" component of the force. In one example, force stability can vary by up to 20% (i.e., +/−20%) for a predetermined blanching period to achieve and maintain sufficient blanching for CRT measurement. With a target force of 5 N, +/−20% allows for +/−1N.

In this example, the force is maintained within +/−0.25 N of the target because the more consistent the force, the easier it is to characterize how CRT varies with the applied force; however, this target is difficult for new users. A well-trained clinician can maintain the force to within 0.05 N over the test interval while a CRT measurement novice may have trouble keeping the pressure within +/−1 N of the target pressure. If a CRT result is to include compensation for force, then a value for the force needs to be included. For a force that is nearly constant (there is almost no time-varying component in the force; that is, the AC component is almost zero), it is clear that the value to include in the compensation is the value of the force and only a single factor needs to be included in the corrective model. While it is possible, in principle, to include multiple factors for force in the corrective model, having a single factor is easier and more reliable.

For example, if the average force is 5 N and it varies by +/−1 N, then while the average force may be 5, it might have been 4 or 6 (or anywhere in between) just prior to release of the force. In this case, a corrective model might need to include statistics about the force applied such as: min. max, average, standard deviation, and perhaps a time-weighted force factor (since force near the end is more important than the force applied at the beginning of the force stability window) In another example, the force stability period is to be maintained for up to twice as long as the blanching stability window period. The blanching stability window period can be up to 0.25 second, so that force stability period is up to 0.5 seconds. This allows for the optical signal to reflect blanch stability prior to force release. Any appropriate time period or duration can be used.

In another example, the duration is equal to or greater than 100 milliseconds (ms) and less than or equal to 5000 ms. A duration less than 100 ms does not provide a true snapshot of the force. A duration greater than 5000 ms is too long to properly evaluate a force. The threshold range can be a value or range of values that fall within a given range or percentage of an average of a maximum and a minimum of the baseline. For example, if a maximum is 1 N and a minimum is 0.5 N, the average is 0.75 N. The threshold range can be +/−10% of the average. The force is considered stable if the calculated force within the sliding window falls within 0.575-0.650 N for a duration of 200 ms.

If the force applied during the time interval of T1 to T2 falls outside of a stable force value or range of stable force values for a given amount of time, then proper blanching has not been achieved and can lead to incorrect results or determinations. The test can therefore be run again. The user or practitioner can be notified accordingly.

The blanch stability can also be determined by a sliding window. In one example, the sliding window applied to blanching is narrower than (i.e., not as wide as) the window for the force baseline. For example, the window can be from 500-1000 ms.

The optical signal magnitude (i.e., amount) and stability are determined in the force application window (T1 to T2) to determine whether or not blanching has been achieved and maintained such that an accurate and reliable CRT measurement can be generated or obtained. The optical stability can be used to determine that blanching has stabilized and is suitable for use in measuring CRT. In one example, the optical signal is examined to determine when it has achieved a maximum. The optical variation in the optical signal during the force application window can also be determined. During the force stability window, the optical signal variation can be, for example, less than 10%, thereby indicating that blanching has stabilized. In another example, blanching can be analyzed as a comparison of received optical signal amount versus an expected amount or a previously received amount.

The optical signal during the initial rest period is obtained, such as by the optical sensor 124. O1 represents the average optical signal during the initial rest period. In other words, O1 represents a baseline value of the optical signal. For example, the average optical signal from a time prior to force application (e.g., 100-5000 ms prior to T1), can be stored for later processing use. Variation of the optical signal within the baseline average can be calculated, such as by tracking the highest and lowest value of the optical signal within the baseline averaging period (e.g., 100-5000 ms).

The optical signal during the force stability window is obtained, such as by the optical sensor 124. Stability of the optical signal during the force stability window is the blanch stability window (i.e., the blanch stability window can be less than the force stability window). O2 represents the average optical signal during the blanch stability window. CRT is the time it takes for the optical signal to return to O1 from O2 upon the release or removal of the applied force. In other words, a timing parameter is based on a characteristic of the force signal based on the applied force and on a characteristic of the optical signal based on the applied force. The applied force can also include the removal of the applied force. For example, the timing parameter includes the amplitude of the force signal that decreases to a CRT threshold at a point in time after removal of the force, and the amplitude of the optical signal, after removal of the force, that is equal to the baseline of the optical signal.

Failures in any measurement, including force application, can cause the system to prompt an operator to perform the test again. The force application duration (T1-T2), optical signal changes prior to T1 (baseline optical stability), optical signal changes from T1 to T2 (blanch stability), force prior to T1 (baseline force), force changes following T1 (amount of force applied), force changes from T1 to T2 (force stability), force changes following T2 (duration of force release), and force following T2 (residual force) are processed to determine whether or not the signals or signal characteristics fall outside of a proper range, thereby rendering the CRT measurement invalid.

For example, force release duration (beginning when the applied force is released or removed and the sensed force drops below Threshold C and ending when the sensed force transitions or meets Threshold D) that exceeds a predetermined amount of time can invalidate the CRT measurement. The residual force due to continued force application can extend the CRT, thereby invalidating the accuracy of the calculation or determination. As another example, insufficient force application or duration can lead to insufficient blanching, thereby reducing the CRT and invalidating the accuracy of the calculation or determination. As yet another example, a force applied during the T1-T2 time interval that falls outside of an accepted force range can affect the CRT due to increased blanching (e.g., force applied is greater than acceptable force application) or decreased blanching (e.g., force applied is less than acceptable force application). The CRT results obtained can be incorrect as the CRT will be less than expected due to decreased blanching or greater than expected due to increased blanching. As another example, improper force release duration can affect the CRT due to substantially the same reasons. A force release duration that is too slow will not trigger the capillary refill time while still permitting refilling to occur.

CRT signal assessment includes two force release times: initiation of force release and termination of force release. These values are used to calculate a force release duration. The CRT measurement can be invalid when the force release duration exceeds a desired duration. In one example, the force release duration is to be less than or equal to 100 ms, as this is 10-30 times less than typical capillary refill durations and therefore reflects a small comparative amount of time. In one example, the force duration release window can be utilized to adjust or shift the CRT, such as to account for a user or practitioner that has a longer force duration release.

In one example, the following table can include valid measurements for CRT calculations or determinations and can be determined by one or more processors using sensor signals.

| Characteristic | Valid Range | Notes |
|---|---|---|
| T2-T1 | 2-5 s | |
| Baseline stability | +/−10% | Within a 3 s window |
| Blanch stability | +/−10% | |
| Baseline force | <0.5N | |
| Force applied | 1.5-4N | |
| Force stability | +/−20% or +/−1N, whichever is less | |
| Force release duration after T2 | <100 ms | |
| Residual force | <0.5N | For a duration of 4 s after T2 |
| Digit Temperature | 22-38 C. | |

In one example. Threshold D can equal the baseline force. In another example. Threshold D can be 1-50% of the average force of the force stability period.

It should be noted that although thresholds have been used to describe the process, the signal processing itself need not rely on static thresholds. Dynamic thresholds (e.g., threshold can be a percent deviation or can meet or exceed a given rate of change) can be employed, whereby the beginning and end of force application can be determined by determining an increase or decrease in the force signal that meets or exceeds a given or pre-determined rate of force signal change (i.e., slope). The rapidity and direction (increase or decrease) of force change can be determined by subtracting a value representing the current force with a force measured at a recent previous time. For example, subtracting a current sample of force from one or more past samples of force. As another example, optical thresholds (static or dynamic) can be employed to calculate the various optical metrics of interest.

The measurement quality is then calculated from an assessment of whether important measurement characteristics, such as those outlined in Table 1, are within desired ranges, and optionally, how close to optimal values the characteristics are. These metrics may be reported for review without further data (e.g., by a clinician), used to trigger a request for re-measurement (if suboptimal), or used to provide a validation (if measurement metrics are acceptable).

CRT is calculated as the time from force release (T2) to the time where the optical signal O2 returns to its baseline value O1 or within a predetermined range or percentage of the optical signal baseline. The return to the baseline value or within the predetermined range or percentage is a blanch-end criterion. The blanch-end criteria can be calculated as a percentage of the difference between the average blanch level and the optical signal baseline O1. The blanch end criteria can be higher than the optical signal baseline O1. When the decreasing optical signal reaches a level matching the optical signal baseline O1 within this range, the optical signal is considered to have returned to baseline O1, with the patient's capillaries having been refilled to their baseline level, such as at time T3. Thus, the capillary refill time can be calculated as T3-T2, or alternatively, T3-T2-(Force Release Duration). The blanch end criteria can also be calculated by an algorithmic fit, such as an exponential decay curve, including an idealized curve. The blanch end criteria can also be calculated with a tracking or trending window, comparable to the sliding window. Though the width of the blanch end criteria window is 10 ms-1 s.

The system may include methods to identify the amount of noise in the signal, classify the noise, and if needed, remove the noise. Methods to classify the noise amplitude include comparing the energy in time and/or frequency range to another time and/or frequency range. For example, comparing the optical energy at less than 0.5 Hz while the pressure is applied to the optical energy above 10 Hz while the pressure is applied or comparing the optical energy before pressure was applied to the optical energy while pressure is applied. Another method may use curve fitting and matched filters where the raw data are fit to a curve and where there are substantial deviations from the curve and subtracted. Matched filters may be advantageous in instances where substantially repetitive signals occur, such as cardiogenic effects. The amplitude of the difference is a measure of the noise. If the noise has the characteristic shape of a pulse, then we may classify it as cardiogenic noise. Analogously, the decrease in optical energy with capillary refill occurring may be well defined in the frequency domain, for example, if the model of the time-domain curve is $\exp(-at)$, then the frequency domain would be $2a/(a^2+f^2)$ and deviations from this would be noise. Noise may be identified and labeled on a set of existing data. With the noise sources classified, then artificial intelligence solutions, such as machine learning may use the labeled data to create neural nets that recognize and classify noise features in new data sets.

Mathematical models or algorithms can be applied to fit the signals to improve the signal to noise ratio. Alternatively, or in combination, one or more filters can be applied to the sensed data or data signals to reduce noise. The noise can be due to a heartbeat of the patient, mechanical factors, motion of the device 100, or the like. For example, an exponential decay signal model can be applied to the optical signal from T2 to T3. The model parameters can be adjusted until a minimum least squares error is reached. The model may then be used to calculate a refined blanch end time based on model projections of the optical signal's time to approach its baseline value. Because blanching will tend to remove fluid from arterioles, venules, capillaries and interstitial spaces, the refilling of blood in the fingertip may require multiple parameters to model.

For example, the arterioles must first refill before the capillaries refill and physics of refilling the arterioles is different than the physics governing the refilling of capillaries, where osmotic pressure is responsible for the flow. Models may include a combination of functions, for example the sum of two exponentials with different time constants, different coefficients, or different bases. In this case, the Padé-Laplace Method of Curve-Fitting Multi-Exponential Decays may be used. Other functions, such as logarithms, polynomials and the like may be included in the model. When filtering is used to remove noise, it may "soften" the start of the decrease in optical signal strength. This softening of the start may in turn affect, for example, the exponential time constant. Softening may be avoided by identifying the start of the decrease, for example by noting the time of pressure release, storing the original data for times near the pressure release, applying a filter to the data and restoring the original data for times near the pressure release.

The capillary refill time may depend on when in the cardiac cycle the pressure is released. For example, if the pressure is released at systole, the blood pressure is higher, resulting in a faster initial refilling than if the pressure is released at diastole. The filter may be low-pass, band-pass, high-pass, notch, or a combination. Filters may be implemented in the time domain, frequency domain, or a combination, for example using wavelets. Filtering algorithms like simple high-pass filtering, wavelet denoising, and Empirical Mode Decomposition (EMD) Based Denoising show superior performance for calculating a cleaned envelope signal. Template Subtraction (TS), including nonlocal Euclidean median (NLEM) may be used. One might fit a model to the data and subtract the model from the data to obtain a model for the noise, which is then subtracted from the original data. A first measurement might be made purely to characterize cardiogenic artifact, from which a matched filter is developed and subsequently used to detect and remove cardiogenic artifact. A system may use a beat picking algorithm to detect when the cardiogenic effects occur and use this as an aid to removing the cardiogenic effects.

When the noise is relatively short compared to the system being analyzed, for example pulses of duration 100 ms over compared to a CRT that decreases over a time of several seconds, then time domain filtering may be advantageously used. For example, by using a moving average window with a time scale on order of the pulse, for example 100 to 500 ms when the decay scale occurs over several seconds will cause the noise signals to be attenuated without significantly altering the time decay of the longer-scale CRT signal. The duration of the moving average filter may be adjusted based on the actual width of the cardiac pulse, for example detected using a matched filter that is tuned to yield a maximum correlation with the CRT artifact that exists in the CRT data.

In the frequency domain, much of the cardiogenic artifact may be removed by implementing a band-stop filter with a center frequency that is nominally the inverse of the pulse width, or a high-pass filter with a cutoff frequency lower than the inverse of the pulse width. For example, if a pulse width is nominally 100 ms, then a bandpass filter centered at 10 Hz would remove a large amount of the energy. Assuming the CRT may be modeled with an exponential decay that has a 2-second time constant, the half-power bandwidth is at $\omega=2*\pi*f=2$ rad/s, or $f=1/\pi$ (about 0.3 Hz). A lowpass filter with cutoff frequency at 1.2 Hz would be three octaves above 0.3 Hz and about 3 octaves below 10 Hz and a suitable band-stop filter to remove cardiogenic artifact might have corner frequencies of 1.2 to 20 Hz.

Alternatively, several measurements might be made and the cardiogenic artifact from each is detected and used to make a matched filter based on an average of the cardiogenic artifact. Other uses of filters may be implemented by those with skill in the art.

Returning to the noise due to a heartbeat, this signal may also be extracted to determine the pulse rate of the patient and the amplitude may be used to derive a perfusion index (PI). Along with CRT, pulse rate and PI may be included with patient data provided to a caregiver, clinician, medical record, electronic medical record, electronic health record or the like.

The PI is a ratio of the AC (pulsatile) to the DC (non-pulsatile or average) blood flow and derivation of PI is well known to those skilled in the art. In current art, PI is only derived from an SPO2 signal, which in turn is based on optical information in red and IR wavelength bands. Using the same methods, this invention considers derivation of a PI from a single wavelength band. This invention also considers derivation of a PI and the derivation of CRT from analysis of video recordings of the patient's skin, such as may be made with Eulerian Video Magnification (EVM). EVM amplifies selected spatial elements within the video frame and may be used to see a color change in the skin that occurs as a fresh pulse of blood arrives at the capillary bed. The magnitude of this color change is directly dependent on the perfusion and may be used to derive a PI. For example, the ratio of the AC (pulsatile) level of green light to the DC (non-pulsatile or average) level of green light. Other methods of measuring PI may be used, such as using the optical return of a laser, which provides a monochromatic, focused light source that can be applied from and detected from a distance. Similarly, if a blanching pressure is applied to the skin area being recorded with video, then the video data may be analyzed to determine CRT.

The PI, whether derived from pulse oximetry (SPO2) or the present invention, is a surrogate for capillary refill time, which is considered the standard for measurements of peripheral perfusion. PI has an advantage that it can be measured continuously and without need for blanching the capillary bed. When a clinician is available to provide blanching, CRT is measured and reported and at other times, perfusion index is measured and reported. If there is a substantial change in the PI or other vital sign (pulse rate, temperature gradient, temperature of the fingertip, etc.), then the system may alert a clinician to make additional vital sign measurements, including of CRT.

The present invention may be considered as an extremely large, single pixel video of the capillary refill bed. Indeed, the size of the single detector is larger than CCD imagers in smart phones. For remote measurement of CRT, video may be applied to analyze the blanching and refill of a capillary bed. For example, if video of an infant's chest is being recorded while a clinician pressed on the sternum, the video will include frames showing the blanched sternum returning to normal color. If the blanching pressure is applied using a standard clinical method, it would be applied via the clinician's fingertips. The blanching pressure is applied by an optically transparent object, allowing the video record to include the skin prior to and during blanching. The video content is analyzed to determine many of the features in the fingertip version of this invention. The motion of the hand/finger/instrument along with variations in the skin color around where the pressure is applied are used to determine the time when force was applied (T1), when pressure is relatively constant, and a measure of the variation in pressure during the force stability window. Motion is also analyzed to determine a time (T2) of pressure release. As with the finger sensor, when the rate of change of the skin color reaches a lower threshold, the algorithm detects that the capillary refill is complete. Alternatively, the skin surrounding the pressure-applied area may be used as a baseline and when the color of the pressure-applied area is within a threshold, for example 5%, of the same as the surrounding area, then the capillary refill time is considered complete. Video stabilization techniques known to those skilled in the art may be used to help ensure that the same pixels are used throughout the CRT evaluation period.

Video, including video with EVM, may be used as part of the analysis to determine when the capillary refill is complete and to measure PI. For example, the AC component of a wavelength of light reflected by the skin can be compared to the DC component, and the ratio of these two is a perfusion index. Advantageously, the analysis of the CRT waveform only includes pixels that changed substantially immediately after the blanching pressure was released. Pixels far from the blanching area will include cardiogenic artifact, which slightly changes the color (less green at systole, for example). Pixels near the blanching area will include cardiogenic artifact and a small amount of change due to the removal of the proximal blanching pressure. Pixels that map directly to the blanching area will have the largest amount of color change due to the removal of the blanching pressure. The pixels to be considered can be determined by cropping to the area where the blanching occurred, for example, by identifying and cropping around the area where the provider's fingertips were applied.

Another method that may be used with cropping or on its own is to evaluate the magnitude of the color change for a specific color (e.g., green) by first filtering the video data to only include light in a specific wavelength band, e.g., 530-540 nm. Other colors, such as red may be used. The pixels that exhibit the largest change in intensity in the selected wavelength band that is correlated with the removal of the blanching pressure will be those where blanching occurred. Another method that may be used to determine the blanching area is by application of an edge detection algorithm to the image. The edge detection algorithm is applied to the data where only the green light (approximately 530-540 nm) remains. By averaging the 530-540 nm data for only the subset of pixels where blanching occurred, the signal-to-noise ratio is increased. Alternatively, the camera of a smart phone in concert with the touch screen may be used to evaluate CRT. By placing a finger over the camera lens (and partially over the LED) and starting a video camera application, the entire imaging sensor records the light that has passed through the skin. As pressure is applied between the screen side and the finger, the finger is blanched. The touchscreen detects an increasing amount of the screen being touched as more pressure is applied. The more constant the area, the more constant is the pressure during the force stability window. That is, the amount of the screen indicating it is being touched is proportional to the applied pressure.

The touchscreen feature also can provide timing of when the pressure was released. The output of the imager is evaluated for changes in color (typically, green). When the color change stops, the CRT is complete. In practical terms, when the color change across a 100 ms observation window is less than a threshold, typically 5%, the CRT is deemed complete. The system advantageously includes only the pixels that include the area that was blanched. For the smartphone camera, it may be that all the pixels image skin that has had blanching pressure applied and there is no need to detect the subset of pixels that image skin that was blanched. When the flash of a smartphone camera is located close to the camera, it could be used to either augment ambient light or provide a source of reflected or partially reflected light from the digit. Using this technique, CRT could also be measured using light reflection on the smartphone.

The capillary refill timer starts when the force is released, as determined by the force sensor, and ends when the optical signal returns to a baseline value or falls within a range of the baseline value. For example, when there is a sudden and monotonically decreasing pressure with a certain change in pressure per unit time (e.g., Pa/s), the system may conclude that the pressure has been released.

If the quality metrics are determined to be invalid, the CRT measurement process can be repeated. However, even if valid, the CRT measurement process can be repeated to establish an average CRT to remove effects of noise and random events, such as the point in the cardiac cycle where the pressure is released, quantization errors in timing, thermal noise, and the like. Various averaging and statistical methods known to those skilled in the art may be employed, such as: averaging, removing outliers, and re-computing an average. When averaging results of measurements that are subject to noise, the number of averages taken and/or statistical methods employed may be a function of the quality metrics, particularly the output quality metrics. For example, a signal with more noise would be averaged more times to decrease the effect of the noise. When CRT data can be aligned, for example, based on a pressure-release criterion, the raw data may be averaged to reduce both random noise (thermal, quantization, etc) and cardiogenic noise. Signal averaging is a technique for increasing the signal-to-noise ratio SNR of an inherently noisy signal: for random noise, by averaging the results of N experiments performed under identical conditions, the SNR increases by a factor of sqrt(N) over the value for a single experiment. The reason is that the total signal is proportional to N. and the standard deviation of the statistical noise increases as sqrt(N). Thus, when the signal average is formed by dividing the total signal by N, the magnitude of the averaged signal remains constant whereas its noise decreases by sqrt(N). An inherently noisy experiment with a small SNR for analysis may achieve a large SNR if it can be repeated enough times.

During the process, an application or program can display signal data and alerts, notifications, indications, or instructions regarding the steps to be performed. For example, a series of smartphone or tablet display updates can be provided. The application or program can also display information associated with the process or collection of data.

The displayed results may take a variety of forms. For example, a CRT measurement time, an averaged CRT, a scaled score, or a related metric, including a color-coded output to indicate healthy CRT versus a CRT that indicates a condition.

The application or program can also link to clinical information or contact information, such as to guide the user, practitioner, or caregiver with next steps.

Another embodiment of the finger sensor includes a battery. CPU, and wireless functionality, which removes the need for the intermediate devices. This embodiment may also support wireless charging. In another embodiment, the finger sensor has a USB interface, which supplies power, and connects directly to a computing device such as a table, laptop, PC, or smartphone, removing the need for an intermediate device. Another embodiment provides network connectivity in the watch, removing the need for a directly connected smartphone. In this embodiment, the intermediate (watch) device can connect directly to the hospital's wireless network (a network such as Wi-Fi, which is based on IEEE 802.11) or, if equipped with a cellular modem, the intermediate device can connect to the hospital network over a cellular connection. Data are then passed to a network-connected computing device, which displays the user interface, provides guidance to the clinician as discussed elsewhere in this specification.

Figure 5:
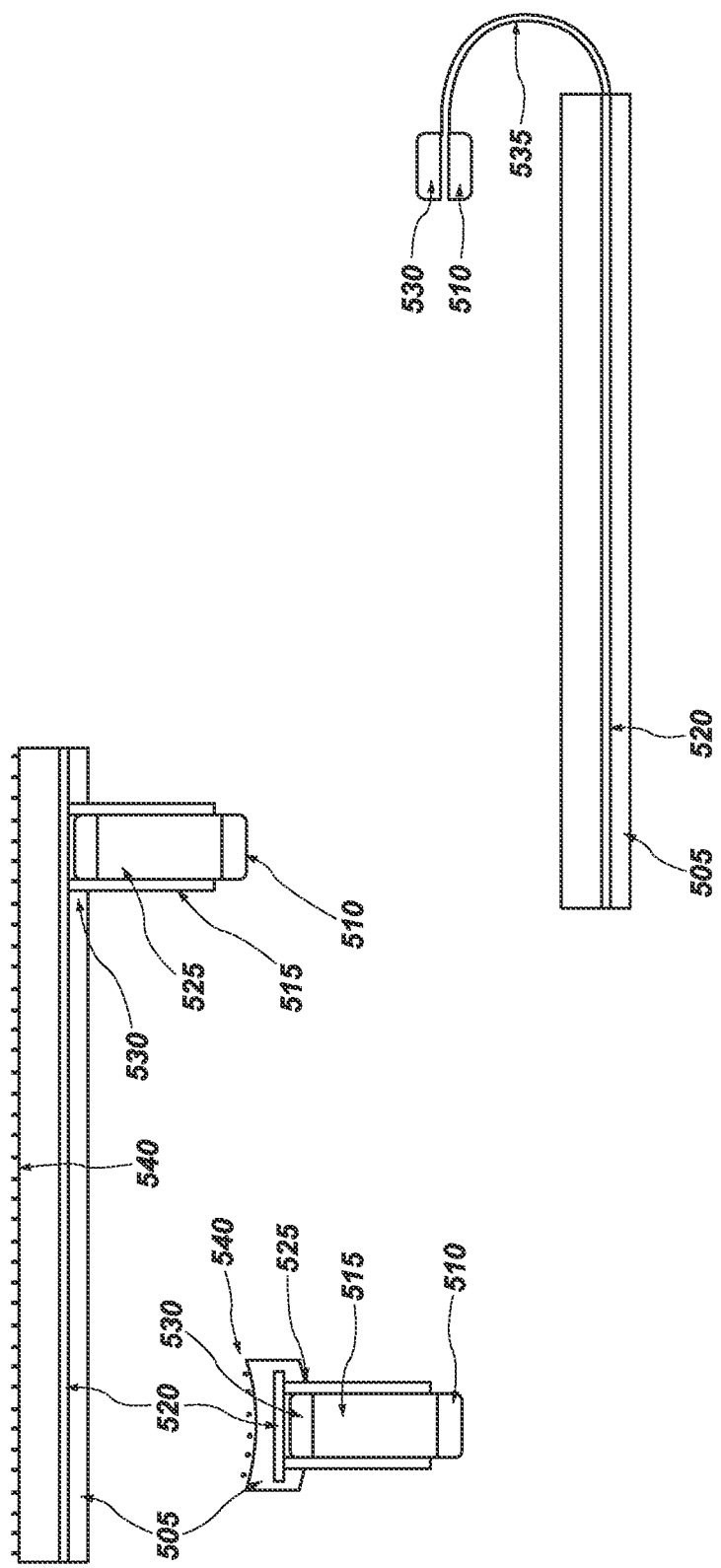
FIG. 5 is a diagram showing two different solutions to provide applied force feedback to the user without use of a force transducer.

Conventional methods reasonably assume that a precise measure of pressure is required to ensure a reliable CRT measurement. However, our research using a continuous and accurate pressure transducer along with pressure-sensitive switches shows that with feedback indicating the user has provided the target pressure, stable pressure application can be achieved. Feedback can be of haptic (touch), optical, or acoustic in nature. Other art assumes that no monitoring of pressure is required. Without any pressure feedback, the pressure may vary nearly 10-fold. At such high pressures the CRT is artificially elongated, which results in an incorrect CRT value. FIG. 5 shows an alternate embodiment in cases where precise measure of the force is not required, providing a method to detect that the force is within limits may be acceptable. Referring to 5: where element 505 is the plastic housing and element 520 is a printed circuit board (PCB), one example of this is a cylinder upon which are attached tactile switches 530 and 510, with different actuation forces, for example 5 N and 6 N, for example the Snaptron GX08500 and GX08600, respectively. Cylinder 525 is guided to move up and down within annulus 515. When depressed, the cylinder-switch assembly (composed of elements 510, 525, 530) moves against PCB 520. Added force causes the 5 N switch to activate, providing tactile feedback to the user that the minimum force has been provided and also a signal to the system that the minimum force has been applied. This force should be maintained for several seconds, until the system alerts the user to release force.

If the minimum force is not maintained, the 5N switch will deactivate, providing tactile feedback to the user and sensor feedback to the system that the force was not maintained. Similarly, if the force exceeds a maximum value (6 N in this example), then the second switch activates, providing tactile feedback to the user that the force has moved outside of the target range and a sensor input to the system that the maximum force has been exceeded. In other examples, the top switch may be mounted to the PCB. In yet other examples, both switches may be mounted to a semi-rigid substrate, such as Kapton with a layer of 1-oz copper (510) providing both a mechanical and an electrical connection to the PCB. Finally, for users who able to provide a sufficiently constant force with only an indication of meeting a first (minimum) force threshold. A pressure sensor such as the 34-00004 model manufactured by Interlink Electronics may be used. This sensor consists of metal traces, the resistance of which changes in a known and repeatable way when pressure is applied. The resistance can be measured and converted into a force. Similar traces as in the 34-00004 sensor may be designed into the PCB that supports the other electronics of the finger sensor to provide a means for pressure measurement without additional parts.

Figure 6:
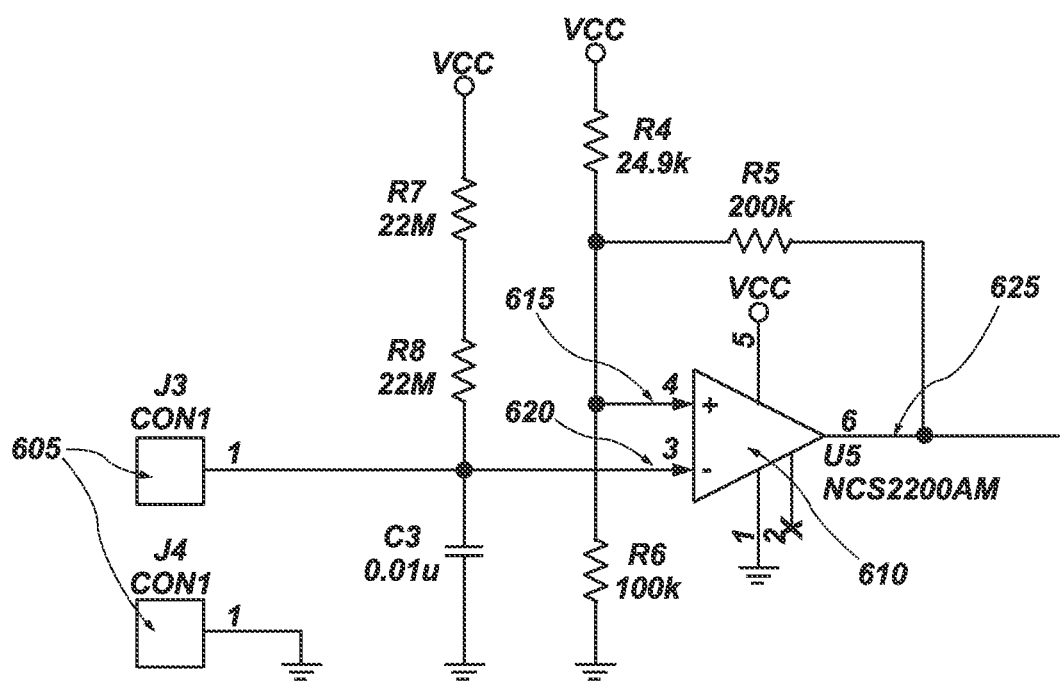
FIG. 6 is a schematic diagram illustrating a circuit that detects a fingertip in contact with the sensor.

FIG. 6 shows a schematic diagram for a circuit to detect when a patient's skin is in contact with both skin-contact sensors 605. Comparator 610 is open loop when no finger is in contact and the output 625 is designed to go to its negative rail in this case, because the full supply voltage is applied to the negative input 620. When a finger makes a connection between electrical contacts 605, the voltage on the comparator's negative input 620 decreases below the voltage on the positive input 615 and the comparator's output 625 changes to positive. Other electronics solutions using transistors and other switching solutions may be used by those skilled in the art. Optical and ultrasonic solutions may also be used to determine that the finger is in contact with the sensor. For example, if no light can pass longitudinally under the fingertip, then fingertip contact with the optical sensor can be ascertained. Ultrasonic solutions can measure the distance from the digit plate 120 to the fingertip and determine the fingertip is in contact with the optical sensor.

In contrast to typical leads-on/leads-off detector used in ECG, where the impedance being detected is relatively low due to the use of wet electrodes, this system must provide a reliable contact measurement for impedance ranges of several million ohms using dry contacts. Also, this system must have the contact 605 in a precise mechanical position (flanking, and approximately 0.5 mm higher than) the optical sensor. For ECG, an electrode that falls off causes the same ECG channel to which the electrode provides a voltage to indicate that the electrode is disconnected. In other words, the "leads off" state is encoded as an analog signal on the same wire that carries the ECG signal. With an optically detected signal, there is not a way to encode the "loss of contact with the skin" state as with ECG.

Figure 7:
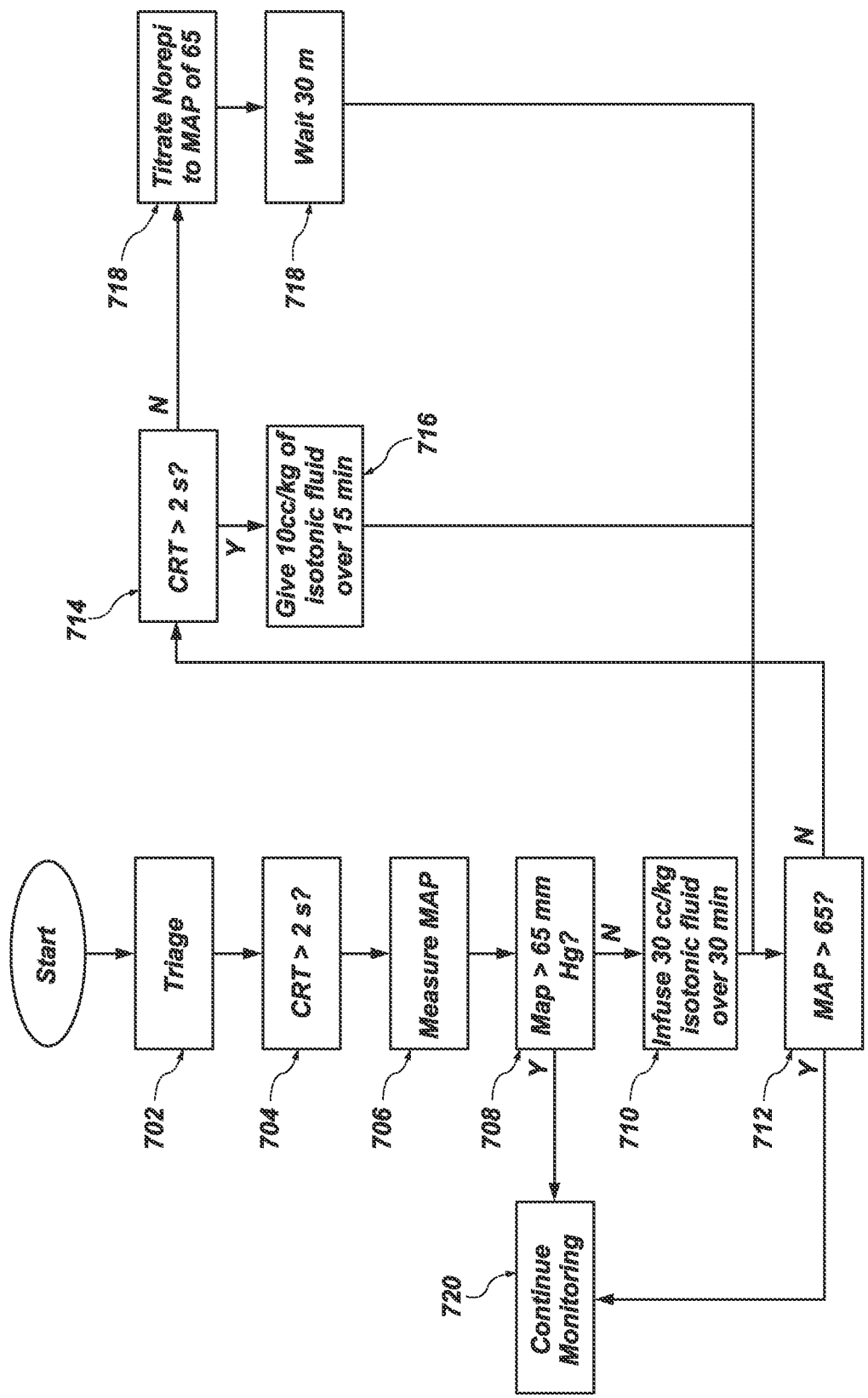
FIG. 7 is a flow diagram illustrating how capillary refill time may be used in a closed-loop infusion monitoring system.

FIG. 7 illustrates a process for closed-loop fluid infusion pump monitoring. In step 702, the patient is triaged and as part of triage, the patient's capillary refill is evaluated in step 704. If the CRT is prolonged, for example, greater the 2 seconds, then the clinician may next measure the mean arterial pressure (MAP) in step 706. Measuring MAP requires connecting a vital signs monitor to the patient. The MAP is evaluated in step 708. If the MAP is sufficiently high, for example, greater than 65 mm Hg, the patient monitoring will continue in step 720 without isotonic fluid infusion. If the MAP is less than or equal to 65 mm Hg, then the patient may be infused with fluids or blood products in step 710. During infusion, the MAP and CRT are repeatedly evaluated in steps 712 and 714, respectively. If the MAP increases above 65 in step 712, then the fluid infusion may be halted, but patient monitoring continues in step 720. If the MAP is less than or equal to 65, then the CRT is evaluated in step 714. If the CRT is >2 s, then additional fluid is given in step 716 and MAP is re-evaluated. If in step 714 CRT is not greater than 2 s, then in step 718. Norepinephrine or another vasoactive medication is titrated. After a 30-min wait, control returns to step 712 to reassess MAP. By continuous monitoring of the CRT, the important data of CRT that guides the cessation of saline and the start of vasopressors can be automatically initiated. This monitoring helps to reduce the volume of fluids the patient receives to protect the patient's lungs. This system can also integrate monitoring from arterial catheters that provide continuous blood pressure measurements.

Figure 8:
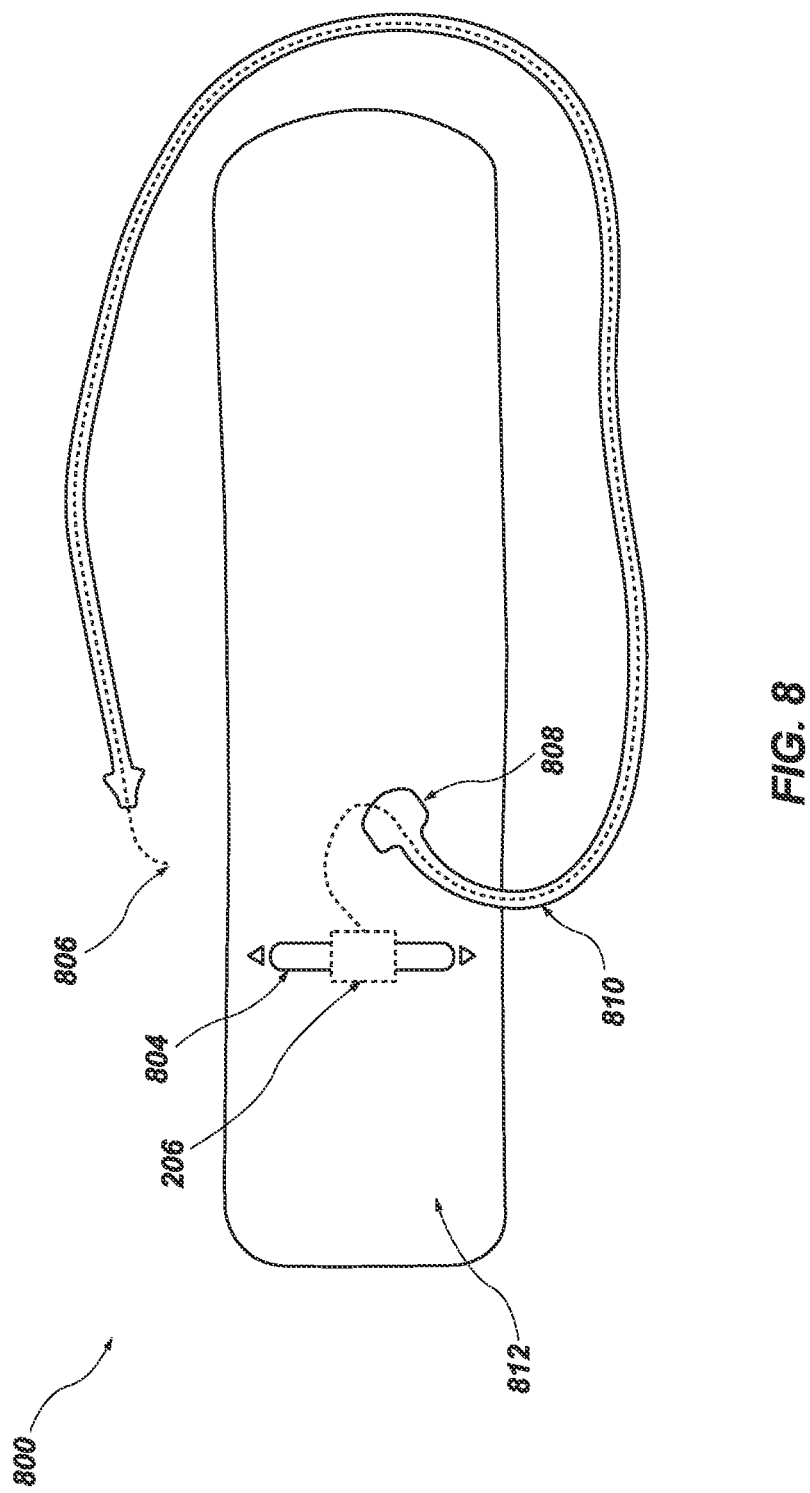
FIG. 8 depicts the present invention integrated as part of a blood pressure cuff.

FIG. 8 shows an integrated blood pressure and capillary refill system. A typical blood pressure cuff is provided pressurized air via a lumen and contains no electronics. Further, the air bladder is made as inexpensively as possible: it is essentially two layers of plastic that are thermally bonded. In this embodiment of the capillary refill sensor, the optical module 206 is built into the bladder 812 of a blood pressure cuff 800. That is, a hole has to be created in the bladder to allow the optical module 206 direct view of the skin, that hole has to be sealed, and the optical module has to be provided power and a way to offload data. Blood pressure measurements are typically kept completely separate because the added complexity and cost to the cuff far outweighs the advantage of adding another sensor, for example, CRT. The senor is embedded in such a way that it has a resilient but flexible backing and similar protection for electrical cables such that the components are resilient to repeated inflation and deflation of the cuff.

It is only because of the recent advances in CRT sensors that allow digital sensing and the concurrent (2021) changes in the surviving sepsis standards that this idea would occur to a team of engineers and scientists immersed in the development of technologies to improve treatment of sepsis. Cuff 800 includes a lumen 810 that is connected at port 808 to bladder 812. Bladder 812 is marked with an "Artery" marker 804, and this marker is set to be visible over an artery (typically the brachial artery). Hence, the side of the cuff opposite the artery marker will be directly against the patient's skin. This location provides a reliable location for placement of optical module 206, which is provided signal and power connections to a host, such as a blood pressure monitor or multi-parameter vital signs monitor, by cable 806 that passes through port 808 and lumen 810. In an alternate embodiment, where disposable cuffs are used, the system may be battery powered and communicate over a wireless means, such as Bluetooth or other means known to those skilled in the art. Such a system may include a method to create a secure connection method, for example by support of NFC, QR code, bar code or other means to enable out-of-band pairing. The system may be enabled by command from the host or by detecting a pressure increase caused by inflation of cuff 812. The system could be powered by the air flow through lumen 810. Blood pressure cuff includes a similar constricting bladder that is not used to measure blood pressure. For example, an air bladder that fits around the tip of a finger. The air cuff has a large orifice to support high air flow rates.

Figure 9A:
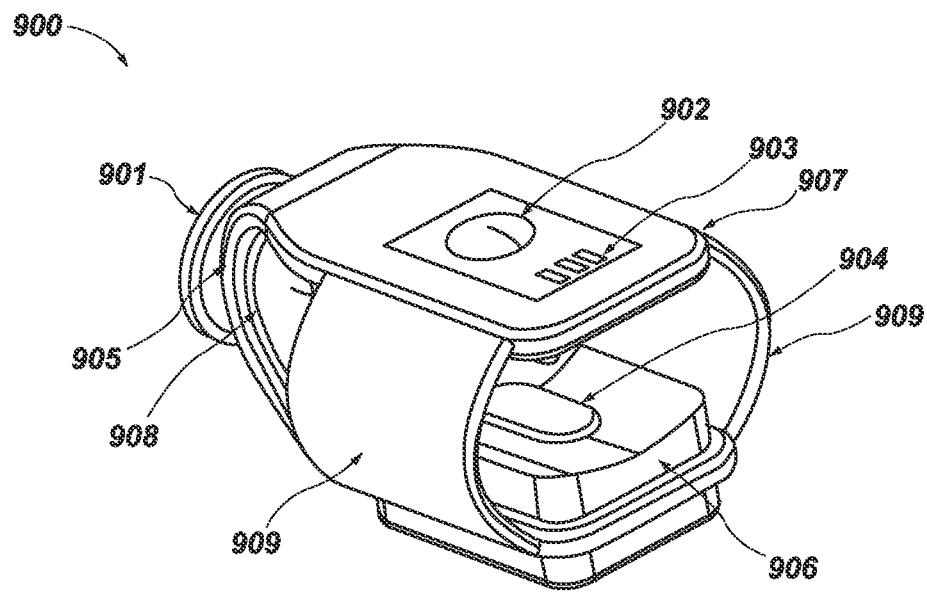
FIGS. 9a and 9b depict the present invention including a mechanism to apply a touch pressure to accommodate various finger sizes using a flat spring.
Figure 9B:
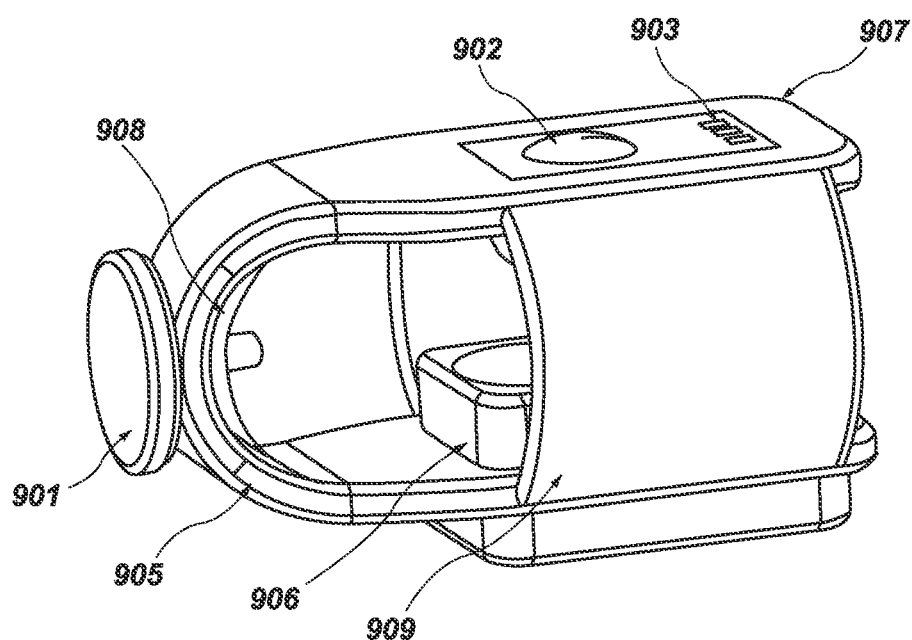

FIGS. 9*a*, 9*b*, 10, and 11 show mechanical embodiments that provide a light shield to block ambient light and a means to apply and adjust the touch pressure. Referring to FIG. 9*a* and FIG. 9*b*, an embodiment of a CRT finger sensor 900 is presented. The touch pressure is adjusted via a ratcheting dial 901 that is connected to a flat spring 908 through the enclosure 905. Sensor enclosure 905 is made of a pliable material that may be deformed and includes a circumferential cover 909 connecting top plate 907 and digit plate 906. The housing prevents ambient light from striking the sensor. Ratcheting dial 901 pushes or pulls against a flat spring 908 and extends both below the digit plate 906 and above the finger (not shown). When ratcheting dial 901 is rotated clockwise, the vertical space between the digit plate 906 and the top plate 907 sensor increases. Conversely, when ratcheting dial 901 is rotated counterclockwise, the vertical space decreases. By rotating ratcheting dial 901 when a finger is inserted into the sensor, the touch pressure may be adjusted, for example by applying a force of 0.2 N from the top plate 907 through the finger (not shown) to the digit plate 906, which includes sensor 904 to detect light and optionally temperature and contact. Digit plate 906 advantageously is curved to assist in centering the finger over the sensor. The overall length of CRT finger sensor 900 is set to help ensure the pad of the finger is centered over the sensor in the longitudinally.

The system may include a pressure sensor to provide a measure of the touch pressure or a force that is proportional to the touch pressure. Alternatively, the user may manually confirm that the touch pressure is properly adjusted, for example by ensuring that when the CRT finger sensor 900 is on the patient's finger and the fingertip is pointed down, the CRT finger sensor 900 remains in place. In another embodiment, the touch pressure is increased just until the skin contact sensors 605 indicate contact. If the skin contact sensors are in contact with the skin for the entire period during with the capillary refill time is determined (from several seconds before the application of blanching pressure until several seconds after release of the blanching pressure when the bland end criteria has been met), the system can determine that the skin was in contact with the optical sensor for the entire duration of determining the CRT. For any time the skin contact sensors indicate no contact, the system may determine the skin was not in contact with the optical detector (meaning there was an air gap between the skin and the optical detector). If such a no-contact period occurred during the time in which the CRT is determined, then the system may determine there is an error in the measurement.

This embodiment also provides a mechanical switch 902 to detect pressure that features hysteresis. The switch activates at a target force, e.g., 6 N and deactivates below that force, e.g., 5 N. The switch may provide a tactile response. The switch's activation and deactivation can be detected by the electronics in the sensor and used to provide one or more of the following: transmit the pressure state to another computing device, such as a smartphone; provide audio feedback from a speaker (not shown) or provide visual feedback. Visual feedback may be provided via LEDs 903. With whatever feedback mechanism is provided, the user is able to determine that the target pressure has been reached and if the pressure has decreased too much below the target pressure. A second switch (not shown) may be added directly under the first switch to provide an overpressure detection. The combination of pressure-activated switches with feedback thus can provide a 3-state indication: Below an acceptable pressure, above an acceptable pressure, and at the target pressure.

Figure 10:
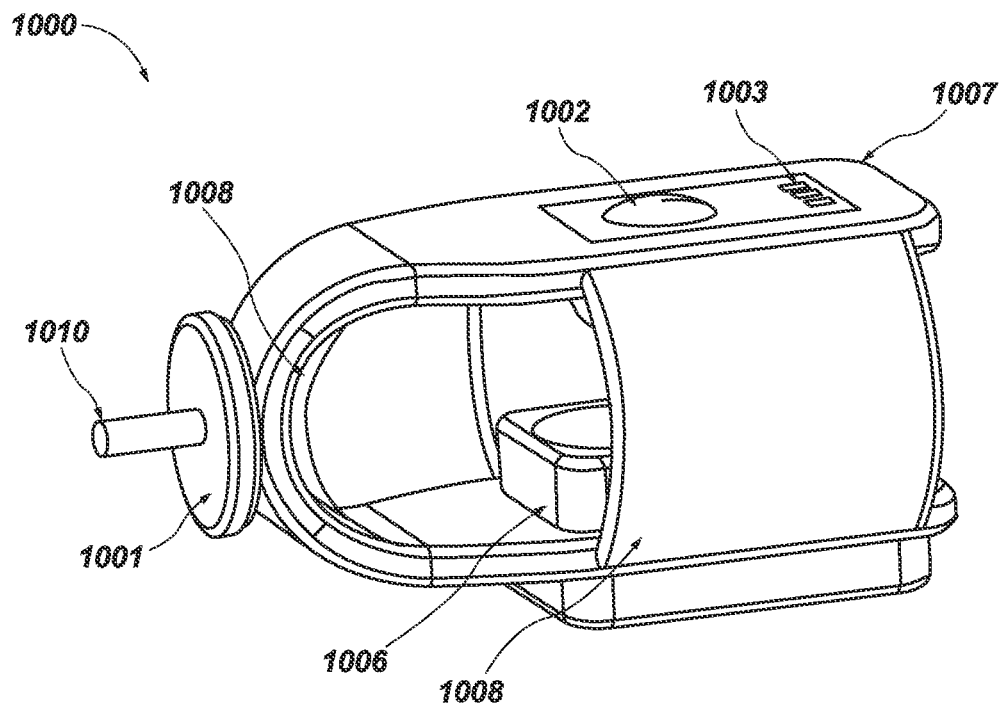
FIG. 10 depicts the present invention including a mechanism to apply a touch pressure to accommodate various finger sizes using a pneumatic mechanism.

Referring now to FIG. 10, the element that provides touch pressure is an air bladder 1008 that also provides the enclosure holding top plate 1007, LEDs 1003, pressure switch 1002 and the digit plate 1006. Element 1001 is a valve with a pneumatic orifice 1010. Valve 1001 may include a bleed valve (not shown) set to avoid pressures above the touch pressure when the air bladder is inflated. By connecting a pump, for example a squeeze ball pump, to the bladder via orifice 1010, the air bladder 1008 may be inflated. The inflated bladder decreases the distance between the top plate 1007 and the digit plate 1006. When a finger is inserted into the sensor, this creates a pressure on the finger. When a proper touch pressure is applied, the closeable relief valve 1001 is closed by the user. The user then applies a blanching pressure and upon release of the blanching pressure, the touch pressure caused by the inflated air bladder 1008 remains so that the optical sensor (not shown) remains in contact with the skin.

Figure 11:
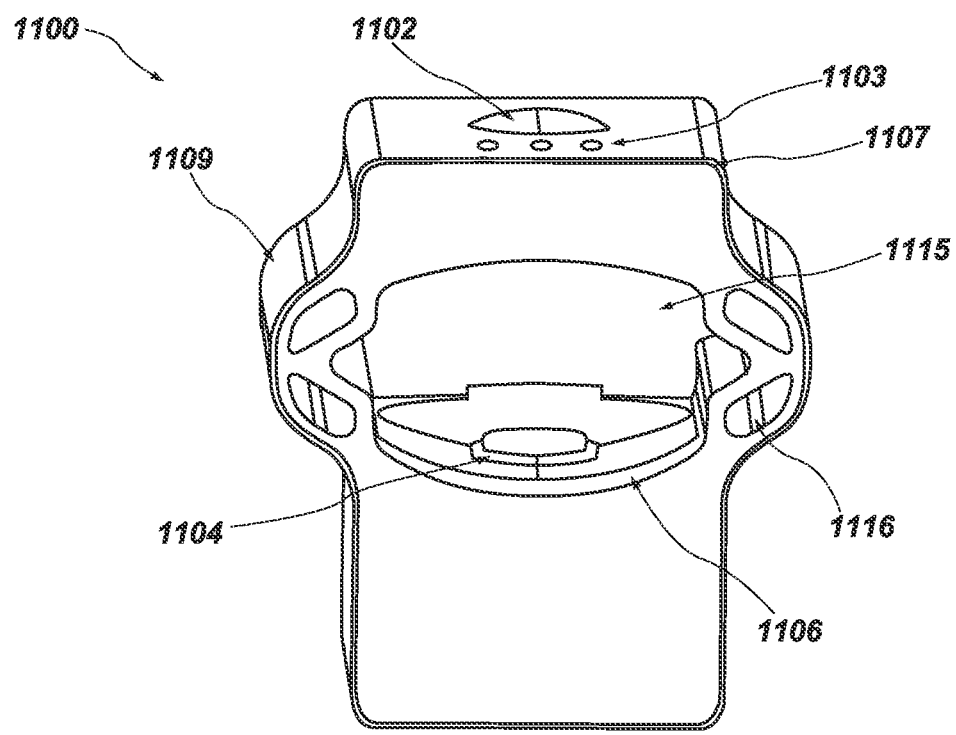
FIG. 11 depicts the present invention including a mechanism to apply a touch pressure using channels in a flexible medium to allow enlargement to accommodate various finger sizes.

For larger fingers, as shown in FIG. 11, longitudinal holes 1116 of various sizes and wall thicknesses, possibly with webbing (not shown) allow the elastomer to expand while keeping the pressure on the fingertip at an appropriate touch pressure, which keeps the fingertip in contact with sensor 1104 that is embedded in curved digit plate 1106. A pressure switch 1102 and LEDs are included in the top plate 1107. Pressure switch 1102 may provide haptic feedback when the target pressure is applied and the switch 1102 closes. The closing switch 1102 allows signaling by various means, including illumination of LEDs 1103, audio, and via a connected smart phone app that can also provide audio, visual, and haptic feedback. LEDs 1103 and other feedback mechanisms may be used for other signaling such as indicating the time remaining until blanching pressure should be applied, the timer remaining until blanching pressure should be released, confirmations of a valid test, indications of error, and the like. Alternatively, the housing may be slightly larger than the finger and the housing is gently pressed to create a touch pressure. A ratchet mechanism stops the housing from expanding and releasing the touch pressure. The ratcheting mechanism is locked prior to application of blanching pressure so that the housing does not tighten during application of the blanching pressure.

Figure 12:
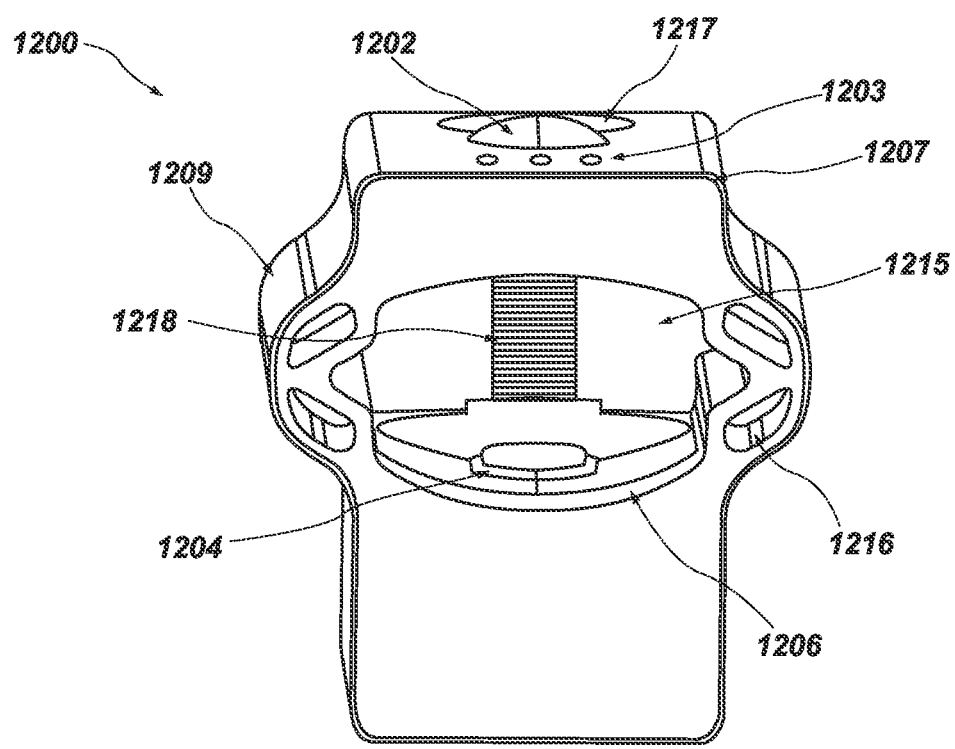
FIG. 12 depicts the present invention including a mechanism to apply a touch pressure using channels in a flexible medium to allow reduction to accommodate various finger sizes.

Referring now to FIG. 12, another embodiment of a CRT sensor 1200 is shown. Enclosure 1209 is made of an elastomer and designed to be slightly larger than the fingertip. The finger is inserted and the user presses on detent 1217 to create a touch pressure. When this happens, lockable ratchet 1218 to close, which will keep the touch pressure even when the user releases pressure on detent 1217. The ratchet may be locked to prevent it from closing further. Back plate 1215 provides a stop so the finger is inserted an appropriate distance with the pad of the fingertip approximately centered on sensor 1204. For smaller fingers, longitudinal holes 1216 of various sizes and wall thicknesses, possibly with webbing (not shown) allow the elastomer to bend as the distance between top plate 1207 and the digit plate while keeping the pressure on the fingertip at an appropriate touch pressure, which keeps the fingertip in contact with sensor 1204 that is embedded in curved digit plate 1206. A pressure switch 1202 and LEDs are included in the top plate 1207. Pressure switch 1202 may provide haptic feedback when the target pressure is applied and the switch 1202 closes. The closing switch 1202 allows signaling by various means, including illumination of LEDs 1203, audio, and via a connected smart phone app that can also provide audio, visual, and haptic feedback. LEDs 1203 and other feedback mechanisms may be used for other signaling such as indicating the time remaining until blanching pressure should be applied, the timer remaining until blanching pressure should be released, confirmations of a valid test, indications of error, and the like.

Though light reflection is discussed, light absorption or transmission can also be determined. Absorption is the inverse of transmission. In other words, a digit having increased light transmission (i.e., more light passes through the digit due to decreased external capillary bed blood flow) has a decreased light absorption (i.e., less light is absorbed when passed through the digit due to decreased external capillary bed blood flow). However, a digit having decreased light transmission (i.e., less light passes through the digit due to increased external capillary bed blood flow) has an increased light absorption (i.e., more light is absorbed when passed through the digit due to increased external capillary bed blood flow).

Though practitioner is discussed, any user is also contemplated, including an end user, an operator, a clinician, a parent, a caregiver, or the like.

Embodiments or examples of the invention can include a non-transitory computer readable medium which can store instructions for performing the above-described methods and any steps thereof, including any combinations of the same. For example, the non-transitory computer readable medium can store instructions for execution by one or more processors or similar devices.

Further embodiments or examples of the present invention can also include the one or more user equipment(s), network sites, backend network, or servers which read out and execute computer executable instructions, such as a non-transitory computer-readable medium, recorded or stored on a storage medium (which may be the same as or different than the storage medium for storing images or files, as discussed above), to perform the functions.

For example, non-transitory computer readable medium can store instructions for execution by one or more processors or similar devices to perform the method of data collection. As another example, non-transitory computer readable medium can store instructions for execution by one or more processors or similar devices to perform data analysis, including CRT calculation and analysis, feedback, quality metric analysis, alerts, notifications, indications, condition determination, treatment determination, the like, or combinations or multiples thereof.

Though certain elements, aspects, components, or the like are described in relation to one embodiment or example, such as an example capillary refill timing system, those elements, aspects, components, or the like can be including with any other capillary refill timing systems, such as when it desirous or advantageous to do so.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments are presented by way of examples for purposes of illustration and description. They are not intended to be exhaustive of or to limit this disclosure to the precise forms described. Many modifications and variations are possible in view of the above teachings. The embodiments are shown and described in order to best explain the principles of this disclosure and practical applications, to thereby enable others skilled in the art to best utilize this disclosure and various embodiments with various modifications as are suited to the particular use contemplated. It is intended that the scope of this disclosure be defined by the following claims and their equivalents:

What is claimed:

1. A system for providing closed-loop feedback of patient fluid state for infusion pump control, comprising:
    an infusion pump having an infusion parameter, the infusion pump configured to deliver a fluid to a patient having a patient fluid state;
    an objective capillary refill time (CRT) measurement component having:
        an optical sensor comprising:
            an optical source, and
            an optical detector configured to generate an electrical signal representative of optical energy received by the optical detector, wherein the optical sensor is configured to generate optical sensor data that includes the electrical signal representative of the optical energy; and
    a processor programmed to:
        receive the optical sensor data from the optical sensor,
        detect an application of and a release of a blanching pressure on patient tissue, the detected application of and release of the blanching pressure based on one or more characteristics of the optical sensor data,
        determine a specific and objective CRT measurement based on the optical sensor data and the detected release of the blanching pressure,
        adjust the infusion parameter of the infusion pump based on the specific and objective CRT measurement, the adjustment of the operating parameter correlating to an adjustment to the patient fluid state.

2. The system of claim 1, wherein the optical sensor data is captured at a first time, and the processor is programmed to repeat the determination of the specific and objective CRT measurement multiple times, the determination of the specific and objective CRT measurement based on the optical sensor data captured at each of the respective multiple times.

3. The system of claim 1, wherein optical sensor data is captured at a first time, and the processor is programmed to repeat the determination of the specific and objective CRT measurement based on the optical sensor data captured at a second time.

4. The system of claim 3, wherein the processor is further programmed to identify a patient CRT trend based on the optical sensor data taken at the first time and the second time.

5. The system of claim 4, wherein the processor is further programmed to generate the instruction to adjust the infusion parameter of the infusion pump based on the patient CRT trend.

6. The system of claim 4, wherein the processor is further programmed to determine a predicted CRT measurement for the patient based on the patient CRT trend.

7. The system of claim 1, wherein the processor is further configured to:

determine a predicted CRT measurement for the patient based on the specific and objective CRT measurement and one or both of a patient characteristic or physiological parameter; and adjust the infusion parameter of the infusion pump based on the predicted CRT measurement.

8. The system of claim 7, wherein the patient characteristic or physiological parameter includes one or more of a patient mean arterial pressure, a patient medication, and a patient demographic.

9. The system of claim 8, wherein the patient medication includes a vasopressor.

10. The system of claim 7, wherein the processor is further configured to generate an alert based on the predicted CRT measurement.

11. The system of claim 7, wherein the processor is further configured to:
    determine the patient fluid state is hypervolemic or is at risk of becoming hypervolemic based on the predicted CRT measurement, and
    generate an alert based on the determination that the patient fluid state is hypervolemic or is at risk of becoming hypervolemic.

12. The system of claim 1, wherein the infusion parameter of the infusion pump includes one or more of the infusion rate per unit mass or the infusion duration.

13. The system of claim 1, wherein the processor is further programmed to generate the instruction to adjust the infusion parameter of the infusion pump based on the specific and objective CRT measurement and a mean arterial pressure of the patient.

14. The system of claim 1, further comprising a communication module, the communication module configured to transmit the specific and objective CRT measurement to a remote device.

15. The system of claim 14, wherein the remote device is a remote monitoring device that includes a physician or nurse smartphone, tablet, or patient monitor.

16. The system of claim 14, wherein the remote device includes an electronic health record (EHR) server.

17. The system of claim 1, wherein the processor is further configured to determine a diagnosis recommendation based on the specific and objective CRT measurement.

18. The system of claim 17, wherein the diagnosis includes one or more of dehydration, sepsis, trauma, and conditions that affect peripheral blood flow.

19. The system of claim 1, wherein the infusion pump includes a controller configured to transmit an instruction to activate the optical sensor to capture the optical data and the processor to determine the CRT measurement.

20. A system for providing closed-loop feedback of patient fluid state for infusion pump control, comprising:
    an infusion pump having an infusion parameter, the infusion pump configured to deliver a fluid to a patient having a patient fluid state;
    a processor programmed to:
        receive optical sensor data from an optical sensor,
        determine a specific and objective CRT measurement based on the optical sensor data, and
        adjust the infusion parameter of the infusion pump based on the specific and objective CRT measurement, the adjustment of the infusion parameter correlating to an adjustment of the patient fluid state.

* * * * *